United States Patent [19]

Schuster et al.

[11] Patent Number: 5,298,509
[45] Date of Patent: Mar. 29, 1994

[54] OCTAHYDRONAPHTHOQUINOLIZINES, AND METHODS OF MAKING AND USING THEREOF

[75] Inventors: David I. Schuster, Wilton, Conn.; Randall B. Murphy, Irvington; Bing Cai, Rego Park, both of N.Y.

[73] Assignee: New York University, New York, N.Y.

[21] Appl. No.: 950,550

[22] Filed: Sep. 25, 1992

[51] Int. Cl.$^5$ .................... C07D 215/16; A61K 31/47
[52] U.S. Cl. ....................................... 514/284; 546/71
[58] Field of Search ...................... 546/71; 514/284

[56] References Cited

U.S. PATENT DOCUMENTS

| | | | |
|---|---|---|---|
| 1,176,597 | 3/1916 | Pictet | 546/71 |
| 3,933,826 | 1/1976 | Kametami | 546/71 |
| 4,128,650 | 12/1978 | Fabre et al. | 546/71 |

OTHER PUBLICATIONS

Mandell, Leon et al., "The Synthesis of Tricyclic Systems with Nitrogen at a Bridgehead," *J. Org. Chem.*, vol. 28, pp. 3440-3442, (1963).

Mandell, Leon et al., "A Conveniant Synthesis of Tricyclic 2-Quinolizidones," *Journal of Org. Chem.*, vol. 29, pp. 3067-6812, (1964).

Bowen, Wayne D. et al., "Metabolites of haloperidol display preferential activity at o receptors compared compared to dopamine D-2 receptors," *European Journal of Pharmacology*, vol. 177, pp. 111-118, (1990).

Gundlach, Andrew L. et al., "Phencycline and o Opiate Receptors in Brain: Biochemical and Autoradiographical Differentiation," *European Journal of Pharmacology*, vol. 113, pp. 465-466, (1985).

Wikstrom, Hakan et al., "N-Substituted 1,2,3,4,4a,5,6,1-0b-Octahydrobenzo[f]quinolines and 3-Phenylpiperidines: Effects on Central Dopamine and o Receptors," *J. Med. Chem.*, vol. 30, pp. 2169-2174, (1987).

Van de Waterbeemd, Han et al., "Quantative Structure-Activity Relationships and Eudismic Analyses of the Presynaptic Dopaminergic Activity and Dopamine D2 and o Receptor Affinities of 3-(3-Hydroxyphenyl) piperidines and Octahydrobenzo[f]quinolines," *J. Med. Chem.*, vol. 30, pp. 1275-2181, (1987).

Gundlach, Andrew L. et al., "Autoradiographic Localization of Sigma Receptor binding sites in Guinea Pig and Rat Central Nervous System with (+)$^3$H-3-(3-Hydroxyphenyl)-N $\propto$ (1-propyl)piperidine," *The Journal of Neuroscience*, vol. 6, No. 6, pp. 1757-1770, (1986).

Mandell, Leon et al., "The Total Synthesis of d,l-Matrine and d,l-Leontine," *Journal of the American Chemical Society*, vol. 87, No. 22, pp. 5234-5236, (1965).

Largent, Brian L. et al., "Structural Determinants of o Receptor Affinity," *Molecular Pharmacology*, vol. 32, pp. 772-784, (1987).

Su, Tsung-Ping et al., "Endogenous Ligands for Sigma Opioid Receptors in the Brain(Sigmaphin): Evidence From Binding Assays," *Life Sciences*, vol. 38, pp. 2199-2210, (1986).

Itzhak, Yossef et al., "Characterization of n-Methyl-4-phenyl-1,2,3,6-tetrahydropyridine (MPTP) Binding Sites in C57BL/6 Mouse Brain: Mutual Effects of Monoamine Oxidase Inhibitors and o Ligands on MPTP and o binding sites," *Molecular Pharmacology*, vol. 39, pp. 385-393, (1990).

Largent, Brian L. et al., "Psychotomimetic opiate receptors labeled and visualized with (+)-[$^3$H]3-(3-hydroxypheny)-N-(1-propyl)piperidine," *Proc. Natl. Acad. Sci. USA*, vol. 81, pp. 4983-4987, (1984).

Largent, Brian L. et al., "Novel antipsychotic drugs share high affinity for a o receptors," *European Journal of Pharmacology*, vol. 155, pp. 345-347, (1988).

Tam, S. William et al., "o opiates and certain antipsychotic drugs mutually inhibit (+)-[$^3$H]SKF 10,047 and [$^3$H]haloperidol binding in guinea pig brain membranes," *Neurobiology*, vol. 81, pp. 5618-5621, (1984).

*Primary Examiner*—Marianne M. Cintins
*Assistant Examiner*—Catherine Scalzo
*Attorney, Agent, or Firm*—Browdy and Neimark

[57] ABSTRACT

Stereoisomeric substituted and/or unsubstituted octahydronaphthoquinolizines (OHNQs), and derivatives and analogs thereof are provided, including pharmaceutical and diagnostic compositions, as well as methods of making and using these compounds according to the following formula I:

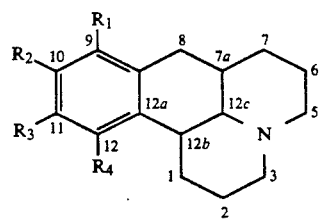

14 Claims, 9 Drawing Sheets

OCTAHYDRONAPHTHOQUINOLIZINES, AND METHODS OF MAKING AND USING THEREOF

FIELD OF THE INVENTION

This invention relates to stereoisomeric octahydronaphthoquinolizines (OHNQs), and derivatives and analogs thereof, including compositions and methods of making and using these compounds.

BACKGROUND OF THE INVENTION

Dopamine,3,4-dihydroxyphenethylamine is a neurotransmitter whose functional role appears to be intimately linked with schizophrenia. The so-called "Dopamine Hypothesis of Schizophrenia" suggested that an overactivity of the mesolimbic/mesocortical ascending dopamine systems in man was etiologic for schizophrenia. This original hypothesis has been extensively modified; although various workers have suggested that imbalances in the activity of other neurotransmitter systems such as serotonin could be involved, recent reviews have all agreed that the dopamine systems do appear in some manner to be intimately involved in schizophrenia.

However, it is not clear if an overactivity per se is involved, and it is probable that the dopamine functional changes alone are not etiologic.

A portion of the difficult lies in the difficulty of concordance in diagnosing schizophrenia, since this term seems to apply to a spectrum of disorders, ranging from affective disorder at one end to chronic paranoid psychosis at the other. Nonetheless, considerable agreement through definitions such as the DSM-IIIr and ICD has been obtained as to the symptomatology which defines the disease. Schizophrenia can be differentiated into two basic categories; that which is amenable to drug treatment, by means of conventional antipsychotic agents, and that which is not, the latter usually being spoken of as "chronic". These categories can to some degree be correlated with the relative balance of positive and negative symptomatology. The role of the negative (Bleulerian) symptomatology, although long known, has in recent years been "rediscovered".

Known neuroleptic agents, regardless of their chemical structures, are pharmacologically active upon the dopamine receptor system, as dopamine antagonists. Many of these compounds, particularly the phenothiazines, also have significant activity on other neurotransmitter systems, in particular various serotonin subtypes, particularly the 5-HT-2, muscarinic receptors, alpha-adrenoceptors, or histamine H-1 or H-2 receptors.

The clinical use of neuroleptics has provided a means for treating patients suffering from psychotic disorders. Short-term use of neuroleptics is indicated in several types of psychotic disorders, e.g., acute psychotic episodes, regardless of type; exacerbations of schizophrenia; acute manic excitement while deferring use of lithium or awaiting onset of its effects; adjunctive therapy for major depression with prominent psychotic symptoms, or when an antidepressant or ECT alone is not successful; for agitation in delirium, dementia, or severe mental retardation while seeking to identify and treat the primary basis of the problem; in certain chronic, degenerative, or idiopathic neuropsychiatric disorders with dyskinesias, such as Huntington's disease or Gilles de la Tourette's syndrome; or for ballism or hemiballism; childhood psychoses or apparently allied conditions marked by severe agitation or aggressive behavior; miscellaneous medical indications, notably nausea and vomiting, or intractable hiccups.

Additionally, continuous long-term use of neuroleptics is indicated in many psychotic disorders, such as (for more than six months) (i) primary indications such as Schizophrenia, Paranoia, Childhood psychoses, some degenerative or idiopathic neuropsychiatric disorders (notably, Huntington's disease and Gilles de la Tourette's syndrome); (ii) secondary indications such as extremely unstable manic-depressive or other episodic psychoses (unusual), otherwise unmanageable behavior symptoms in dementia, amentia, or other brain syndromes; and (iii) questionable indications such as chronic characterological disorders with schizoid, "borderline," or neurotic characteristics; substance abuse; or antisocial behavior, recurrent mood disorders. See, e.g., Baldessarini, *Chemotherapy in Psychiatry*, Revised and Enlarged Edition, Harvard University Press, Cambridge, Mass., (1985), the contents of which is entirely incorporated herein by reference.

Neuroleptics are also referred to as neuroplegics, psychoplegics, psycholeptics, antipsychotics and major tranquilizers, but are sometimes distinguished from non-neuroleptic anti-psychotics. Neuroleptics have recently been characterized as an agent that produces sedative or tranquilizing effects, and which also produces motor side effects, such as catalepsy or extrapyramidal symptomatology. Nonlimiting representative examples of neuroleptics include phenothiazine derivatives (e.g., chlorpromazine); thioxanthine derivatives (e.g., thiothixene); butyrophenone derivatives (e.g., haloperidol); dihydroindolone (e.g., molindone); dibenzoxazepine derivatives (e.g., loxapine); and "atypical" neuroleptics (e.g., sulpiride, remoxipiride pimozide and clozapine). See Berstein *Clinical Pharmacology* Littleton, Mass.: PSG Publishing (1978); Usdin et al *Clinical Pharmacology in Psychiatry* New York:Elsevier North-Holland (1981); and Baldessarini, supra, (1985): and, which references are herein entirely incorporated by reference.

The term "atypical neuroleptics" has been used to describe antipsychotic neuroleptics that produce few or no extrapyramidal side effects and which do not cause catalepsy in animals (See, e.g., Picket et al, *Arch. Gen. Psychiatry* 49:345 (May 1992). Alternatively, atypical neuroleptics, such as clozapine, have been described as those neuroleptics which have a higher affinity for $D_4$ and $D_1$ sites than for $D_2$ sites (See, e.g., Davis et al *Amer. J. Psych.* 148:1474, 1476 (November 1991).

The long term use of all known anti-psychotics, such as neuroleptics or non-neuroleptic antipsychotics, has resulted in serious side effects, as present in Table III, such as persistent and poorly reversible motoric dysfunctions (e.g., tardive dyskinesia) in a significant number of patients.

TABLE III

Neurological Side Effects of Neuroleptic-Antipsychotic Drugs

| Reaction | Features | Period of maximum risk | Proposed mechanism | Treatment |
|---|---|---|---|---|
| Acute dystonia | Spasm of muscles of | 1–5 days | Dopamine excess? | Antiparkinsonism agents are |

TABLE III-continued

Neurological Side Effects of Neuroleptic-Antipsychotic Drugs

| Reaction | Features | Period of maximum risk | Proposed mechanism | Treatment |
|---|---|---|---|---|
| | tongue, face, neck, back; may mimic seizures; not hysterical | | Acetylcholine excess? | diagnostic and curative (i.m. or i.v., then p.o.) |
| Parkinsonism | Bradykinesia, rigidity, variable tremor, mask-facies, shuffling gait | 5–30 days (rarely persists) | Dopamine blockade | Antiparkinsonism agents (p.o); dopamine agonists risky? |
| Akathisia | Motor restlessness; patient may experience anxiety or agitation | 5–60 days (commonly persists) | Unknown | Reduce dose or change drug low doses of propranolol;[a] antiparkinsonism agents or benzodiazepines may help |
| Tardive dyskinesia spontaneous | Oral-facial dyskinesia; chloreo-athetosis, sometimes irreversible, rarely progressive | 6–24 months (worse on withdrawal) | Dopamine excess? | Prevention best; treatment unsatisfactory; slow remission |
| "Rabbit" reduce syndrome | Perioral tremor (late parkinsonism variant?); usually reversible | Months or years | Unknown | Antiparkinsonism agents; dose of neuroleptic |
| Malignant antiparkinsonism syndrome bromocriptine variable; | Catatonia, stupor, fever, unstable pulse and blood pressure; myoglobinemia; can be fatal | Weeks | Unknown | Stop neuroleptic; agents usually fail; often helps; dantrolene general supportive care crucial |

[a]There may be an increased risk of hypotension on interacting high doses of propranolol with some antipsychotic agents; clonidine may also be effective at doses of 0.2–0.8 mg/day, but carries a high risk of hypotension (Zubenko et al., Psychiatry Res. 11:143, 1984).

These sides effects are especially prevalent in geriatric populations, and adequate pharmacological treatment of these debilitating motoric dysfunctions is not currently available. This problem has severely limited the long-term, clinical administration of these agents.

In addition, clozapine, although apparently capable of producing less motor side effects, can cause irreversible, potentially fatal agranulocytosis in a minority of patients administered the drug. Such serious side effects limit the use of clozapine to patients who are resistant to treatment with other neuroleptics.

In the great majority of patients who do respond to the conventional neuroleptics, the clinical response, regardless of the measure used, is highly and significantly correlated with the affinity of the compounds upon $D_2$ dopamine receptors. This correlation, which was first noted by Seeman and his colleagues in the mid-1970s, has been used as a principal supporting argument for the validity of the dopamine hypothesis of schizophrenia.

However, a minority of patients with very severe symptoms, responds poorly if at all even to elevated doses of the conventional antipsychotic agents. It has been found that clozapine, a drug recently reintroduced to clinical practice in this country after original withdrawal due to its association with a small number of cases of severe and fatal agranulocytosis, is highly effective on a majority of this subset of drug-resistant patients. Interestingly, clozapine is not potent as an antagonist for the dopamine $D_2$ receptor, although it does have increased affinity for other dopamine receptor subtypes, such as the $D_4$. Importantly, the drug has a mix of 5-HT-2 and $D_2$ activity which appears to, at least in part, make it desirable as an antipsychotic. However, its potential for toxicity limits its widespread use, and makes its application to these patients expensive, as their blood CBCs must continually be monitored. Thus, the lack of a substance similar in actions to clozapine is a severe deficiency in the related art, and attempts to find such derivatives through structure-activity relationships, molecular modeling, and the like have not yielded clinically useful compounds.

A second and severe deficiency in the prior art is that all classical neuroleptic agents, as exemplified by the butyrophenones and phenothiazines, can upon long-term administration produce severe motoric symptomatology, termed tardive dyskinesia. These motor movements are uncontrollable and can range from relatively trivial manifestations to total debilitation. Tardive dyskinesia is usually poorly reversible upon discontinuation of the chronic neuroleptic, and pharmacological intervention for treatment of tardive dyskinesia itself is only moderately successful. Such motor abnormalities are known to occur in as high as 10% of the patients who are maintained on these drugs for several years; the incidence is much greater in certain groups, such as middle-aged females.

There is therefore a great need for drugs which can be termed "atypical" or "nonclassical" neuroleptics, wherein these agents will treat the symptomatology of schizophrenia either in cases which are resistant to other drugs, without toxic side effects, or whose long-term administration will not produce such toxic side effects.

One system which can be linked to the ascending mesolimbic dopamine system in a functional manner is the sigma receptor.

Sigma receptors were first postulated by Martin et al. (J. Pharmacol. Exp. Therap. 197:517–532 (1976)) to account for the behavioral effects in dogs of N-allylnormetazocine (NANM, SKF 10047)). Sigma receptors are not typical opiate receptors since the binding of sigma ligands (e.g., ($^3$H)-NANM) is not blocked by typical opiate receptor antagonists such as naloxone, and the enantioselectivity of NANM and other opiates for sigma sites ((+)-NANM more potent than (−)-NANM) was opposite to that seen at conventional opiate receptors. See, e.g., Walker, J. M. et al. Pharmacol. Rev. 42:355–737 (1990); Snyder, S. H. et al. J. Neuropsychiatry 1:7–15 (1989); Largent, B. L. et al. Eur. J. Pharmacol. 155:345 (1988).

It was originally thought that benzomorphans, such as NANM, bound to the same receptor site as phencyclidine (PCP), suggesting PCP receptors mediated the psychotomimetic actions of sigma ligands. See, e.g., Mendelsohn et al *J. Pharmacol. Exp. Therap.* 233:597–602 (1985). However, subsequent investigations showed that ($^3$H)-NANM) labels two sites. The first site was a PCP binding site representing a component of the receptor for the excitatory amino acid N-methyl-D-aspartate (NMDA); the second site was not labeled with ($^3$H)-PCP or its analogue ($^3$H)-TCP, but was labeled with high affinity by ($^3$H)-haloperidol and (+)-($^3$H)-3-(+)-3-(3-hydroxyphenyl) N-(1-propyl)-piperidine (+)-($^3$H)-3-PPP. (Tam, S. W. (1983) "Naloxone-inaccessible sigma receptor in rat central nervous system" *Proc. Natl. Acad. Sci. USA* 80, 6703–6707; Largent, B. L. et al. (1986) "Pharmacological and autoradiographic discrimination of sigma and phencyclidine binding sites in the brain with (+)-SKF10047, (+)-($^3$H)-3-PPP and ($^3$H)-1-((2-thienyl)cyclohexyl)-piperidine" *J. Pharmacol. Exp. Therap.* 238, 739–748; Martin, W. R. (1984) "Pharmacology of opioids" Pharmacol. Rev. 35, 283–323). ($^3$H)-NANM binds with low affinity to the PCP site and with high affinity to the latter site, hereafter designated as the sigma-haloperidol or sigma "receptor". The two sites are readily differentiated by radioligand displacement and autoradiographic localization studies. See, e.g., Gundlach et al. *Eur. J. Pharm.* 113:465–466 (1985); Largent et al *Neurobiol.* 81:4983–4987 (1984); Gundlach et al *J. Neurosci.* 6:1757–1770 (1986) McLean et al *Neuroscience* 25:159–269; Aaronsen et al Synapse 4:1–10 (1989). The discovery of sigma receptors, but not PCP receptors, in certain cultured cell lines is further evidence that they are separate and distinct entities. See, e.g., Yang et al *Eur. J. Pharm.* 164:607–610 (1989); Hellewell et al *Brain Res.* 527:244–253; Bowen et al *Eur. J. Pharmacol.* 163:309–318 (1989); Musacchio et al *Life Sci* 45:1721–1732 (1989).

In their exhaustive review of the literature on sigma receptors, Walker et al (Pharmacol. Rev. 42:355–737 (1990)) summarize evidence of the correlation between binding affinity to sigma sites and several functional assays, as well as endogenous ligands for sigma receptors. Su et al. *Life Sci.* 38:2199–2210 (1986) and Tam et al *Eur. J. Pharm.* 193:121.

Of potentially great importance is the finding that atypical antipsychotic drugs have moderate to high affinity for sigma receptors labeled by ($^3$H)-haloperidol and (+)-($^3$H)-3-PPP. These include a group of piperazine (BMY 14802, BMY 13980, rimcazole, tiospirone and cinuperone), a tetrahydro-$\beta$-carboline (WY 47,384) and the benzamide remoxipride. Rimcazole, remoxipride and BMY 14802 show 10 to 15-fold greater selectivity for sigma versus dopamine D2 receptors, and have little or no affinity toward PCP sites. Haloperidol itself binds with very high affinity to the sigma site. Tam et al *Proc. Natl. Acad. Sci. USA* 81:5618–5621 (1984).

An earlier approach to the search for new types of antipsychotics was to seek compounds which interact at dopaminergic autoreceptors, thus inhibiting the release of dopamine into the synapse rather than blocking postsynaptic receptors. (See, e.g., Carlsson, *J. Neural. Transm.*, 47:309 (1983); Hacksell et al., *J. Med. Chem.*, 24:1475 (1981); Johansson et al., *J. Med. Chem.*, 28:1049 (1985); and Svensson et al., *J. Neural. Transm.*, 65:29 (1986). The most promising compound of this type was 3-PPP, which was later found to have higher affinity for sigma receptor sites than for dopaminergic receptors. Largent et al *Proc. Natl. Acad. Sci. USA* 81:4983–4987 (1984).

Walker et al, supra, conclude that the establishment of a role for sigma receptors in psychosis could have profound implications for drug therapy.

The structural diversity of compounds which bind with high affinity to sigma receptor sites is very great, including butyrophenones such as haloperidol and buspirone (but not spiperone), psychotomimetic benzomorphans, and simple 3- and 4-phenylpiperidines. Walker et al., supra.

As part of a broad study of structural determinants of sigma receptor affinity, Largent et al, supra and Wikström et al (*J. Med. Chem.* 30:2169–2174 (1987)) found that a variety of analogs of 3-PPP were potent in inhibiting binding of ($^3$H)-3-PPP to rat brain membranes. In particular, Largent and Wikström found that compounds with larger N-substituents generally exhibited greater sigma affinity, suggesting lipophilicity was an important factor influencing binding to sigma receptors in this system. However, enantiospecific effects on biological activity were small. A considerable variety of substituents could be tolerated on the aromatic ring. Hydrogen bonding did not appear to be a prerequisite for binding to sigma receptors, as it is for binding to dopamine receptors. Largent and Wikström also assayed a series of octahydrobenzo-(f)quinolines, which are somewhat more conformationally constrained tricyclic analogues of 3-PPP. Many of these octahydrobenzo-(g)quinolines were found to be potent sigma ligands. Again, increased lipophilicity enhanced sigma potency, while compounds with methoxy substituents on the aromatic ring were more potent than hydroxy analogues. In this series of compounds, considerable stereoselectivity was now observed. Trans-fused octahydrobenzo-(f)quinolines were generally more potent than cis-fused analogues, and trans octahydrobenzo-(f)quinolines with (4aR, 10bS) stereochemistry were considerably more potent than their enantiomers (e.g., (4aS, 10bR)). In one case examined in the cis series, modest enantiospecificity (2:1) was observed. However, since trans-fused octahydrobenzo-(f)quinolines have strong agonist affinity for pre- and postsynaptic sites on D2 receptors in contrast to the weak D2 affinity of cis-fused octahydrobenzo-(f)quinolines, Largent et al (1987) suggested that the goal of finding sigma-selective ligands which are virtually devoid of D2 affinity could best be achieved with analogues of cis-fused octahydrobenzo-(f)quinolines.

Accordingly, there is a need to provide novel compounds whose stereoisomers will possess a range of effects on sigma, dopamine ($D_1$, $D_2$, $D_3$, $D_4$) and related receptor proteins, and which may modulate such receptors for use in diagnostic, therapeutic and research applications, and as alternative neuromodulating agents.

SUMMARY OF THE INVENTION

It is an object of the present invention to overcome one or more of the deficiencies of the related art.

It is another object of the present invention to provide novel stereoisomeric octahydronaphthoquinolizine (OHNQ) compounds and other, compositions and methods involving octahydronaphtho-quinolizine compounds, and analogs and derivatives thereof, as receptor ligands and/or modulators for in vitro, in situ, and in vivo, diagnostic, therapeutic and research applications, including, but not limited to, alternative compounds that bind "receptors", exemplified by sigma receptors but including the non-limiting examples of opiates ($\mu$, $\delta$, $\alpha$), antipsychotics, antidepressants, antihistamines (H-1, H-2), PCP- and NMDA-related compounds, steroids, dopaminergics ($D_1$, $D_2$, $D_3$, $D_4$, $D_5$), adrenergics ($\alpha_1$, $\alpha_2$, $\beta_1$, $\beta_2$), serotinergics (5-HT-1a, 5-HT-1b, 5-HT-1d, 5-HT-2, 5-HT-3), cholinergics ($M_1$, $M_2$), amino acids and related drugs, guanidines, peptides (substance P, Tachykinins, CCK, Bombesin), channel blockers (Ca+- N-type and L-type), and the like, e.g., as presented in Walker et al *Pharmocol. Reviews* 42:355–402 (1990), the entire contents of which is herein incorporated by reference.

Accordingly, one aspect of the present invention lies in the discovery of OHNQ compounds according to formula (I) which bind sigma receptors with relatively high affinity, such that OHNQs of the present invention provide receptor ligands and/or modulators that may stereospecifically modulate the biological activity of receptor proteins and adjacent biologically active molecules in vitro, in situ and in vivo.

As a non-limiting example, OHNQ compounds and/or compositions may be used in methods for the prevention and treatment of schizophrenia and neurological disorders, such as Gilles de la Tourette's Syndrome, dystonias, choreas and Parkinsonism, as well as other diseases associated with abnormal neuroreceptor modulation. Such methods of the present invention may include administering an effective sigma, dopamine or other receptor modulating amount of an octahydronaphthoquinolizine (OHNQ), and a pharmaceutically effective carrier or diluent.

A further object of the present invention is to provide compounds, compositions and methods for modulating sigma, dopamine or other receptor functions in a subject, including a mammal or a bird, such as a human.

Still another object of the invention is to provide compounds, compositions and methods for selectively modulating or regulating sigma, dopamine or other receptor function in a subject with less selective or non-selective clinical side effects, such as side effects produced by known neuroleptics.

A further object of the invention is to provide pharmaceutical preparations containing octahydronaphthoquinolizines, according to formula I, in an amount sufficient for use in one or more of the embodiments of this invention.

According to one aspect of the present invention, octahydronaphthoquinolizine compounds are provided according to formula (I):

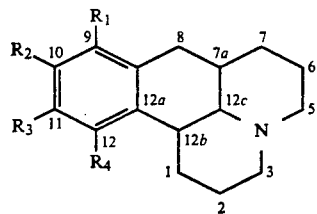

wherein $R^1$, $R^2$, $R^3$ and $R^4$ are the same or different as hydrogen, hydroxy, fluoro, trifluoromethyl, or a $C_{1-10}$ alkoxy optionally substituted with at least one alkyl or phenyl group.

According to another aspect of the present invention, a compound according to formula (I) is provided wherein the compound is in a substantially homogeneous, stereochemically specific formula selected from (trans,trans), (trans,cis), (cis,trans) and (cis,cis).

Other objects of the invention will be apparent to skilled practitioners from the following detailed description and examples of the invention provided below.

BRIEF DESCRIPTION OF THE DRAWINGS

FIG. 9A is an IR spectrum for (cis,cis) OHNQ. FIG. 9B is an IR spectrum for (trans,trans) OHNQ. FIG. 9C is an IR spectrum for (cis,trans) OHNQ. FIG. 9D is an IR spectrum for (trans,cis) OHNQ.

DETAILED DESCRIPTION OF THE INVENTION

Figure 1:
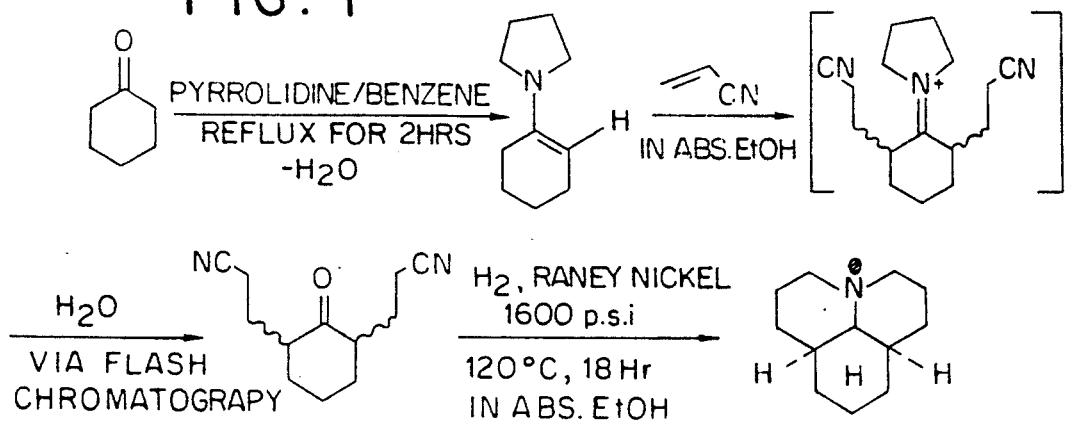
FIG. 1 represents synthetic scheme for tricyclic amines by the route of Mandell et al.

Octahydronaphthoquinolizines (OHNQs) and derivatives may include compounds according to formula (I):

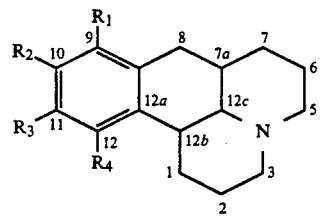

wherein $R^1$, $R^2$, $R^3$ and $R^4$ are the same or different, as hydrogen, hydroxy, fluoro, trifluoromethyl, or a $C_{1-10}$ alkoxy which can be substituted with alkyl or phenyl groups. OHNQs of the present invention have also been discovered to interact and/or modulate, quantitatively and/or qualitatively, sigma receptors, dopamine receptors and functionally as related receptors and/or associated molecules (as defined supra).

Structural features of the OHNQ ring system, along with functional substituent groups and stereoisomers of compounds according to formula (I), make OHNQs useful as therapeutic and diagnostic agents for pathologies associated with sigma, dopamine and other receptor proteins, such as psychiatric and neurological disorders, as a non-limiting example.

The rigidity and eight stereoisomeric forms (four diastereomers, each having a pair of enantiomers) of OHNQs of formula I, according to the present invention, provide compounds with selective sigma receptor affinity, expected to be higher than, e.g., that found for the tricyclic octahydrobenzo-(f) quinolines as modulators of neuroreceptors. Molecular modeling studies using a program such as MACROMODEL®, INSIGHT®, and DISCOVER® show that the spatial requirements and orientation of the orbital containing the lone pair of electrons on the nitrogen vary from one stereoisomer to another in OHNQs according to the present invention. Such OHNQ compounds of the present invention thus provide selective qualitative and quantitative potency at sigma and other neuroreceptor sites.

Synthesis of OHNQs may be achieved by methods of the present invention using known method steps, without undue experimentation, based on the teaching and guidance presented herein. As a non-limiting example, a three-step route as described herein may be used to synthesize a OHNQ compound or derivative of the present invention. Biological activity, including modulation of sigma receptor functions, of OHNQ compounds and compositions of the present invention, at a variety of sigma receptor sites, may be determined by one of ordinary skill according to the present invention without undue experimentation.

OHNQs may be used according to one aspect of the present invention, as a new generation of drugs which possess sigma receptor ligand specificity, consistent with clinical utility in the treatment of sigma receptor related pathologies, such as schizophrenia and other disorders associated with neuroreceptor pathology. As a non-limiting example, OHNQ compounds and derivatives may be used as antipsychotic agents, which lack, or have substantially reduced, side effects relative to known neuroleptics, such as acute extrapyramidal effects or chronic tardive dyskinesia.

OHNQs of the present invention may also be used for treating a variety of other psychiatric syndromes, for which the continued use of known agents, such as phenothiazines and haloperidol, suffer from undesired side effects. OHNQ compounds of the present invention may also be used to treat schizoaffective disorders, which are currently treated with combinations of antidepressants and neuroleptics, as well as panic disorders, which are treated acutely with anixolytics or chronically with drugs such as fluoxetine.

Further, since sigma-selective drugs are known to prevent neurologic damage caused by ischemic insults, OHNQs may also be used to treat chronic cerebrovascular insufficiency or acute cerebrovascular infarction or vascular occlusion. The above pharmacological uses of OHNQs may be provided by one of ordinary skill based on the teaching herein, without undue experimentation.

Since the OHNQ ring system contains three stereogenic (chiral) centers, OHNQ compounds according to formula (I) of the present invention exist in at least eight stereoisomeric forms: four diastereomers (cis,cis; cis,-trans; trans,cis; trans,trans), each of which exists as a pair of enantiomers (i.e., mirror image forms). Therefore, the stereoisomeric form and substituent groups of an OHNQ, according to formula I, may be used in the present invention to qualitatively and/or quantitatively modulate sigma, dopamine and other receptor molecules, as defined supra, and related or functionally associated molecules, biological activity in vitro, in situ and/or in vivo, as a result of receptor specificity provided by a stereoisomeric form of, and/or the presence of substituent groups on, the OHNQ ring system. Such a compound according to formula (I) thus provided sigma, dopamine or other neuroreceptor modulation, which specificity and effects can be determined by known methods without undue experimentation.

Chemical structures of non-limiting examples of OHNQs according to formula (I) are presented below, and include OHNQ (compound I-1), 9-hydroxy OHNQ (I-2), 10-hydroxy OHNO (I-3), 9-methoxy OHNQ (I-4), 10-methoxy OHNQ (I-5), 9-fluoro OHNQ (I-6), 10-fluoro-OHNQ (I-7), 9-trifluoromethyl OHNQ (I-8), 10-trifluoromethyl OHNQ (I-9), 9-,10-dihydroxy OHNQ(I-10) and 9-,10-dimethoxy OHNQ (I-11). Such examples, and further non-limiting examples, are presented as follows:

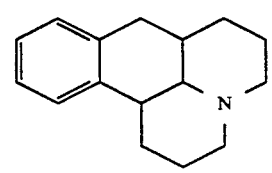

I-1

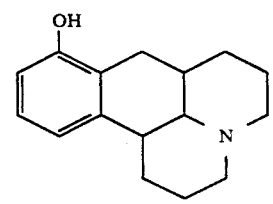

I-2

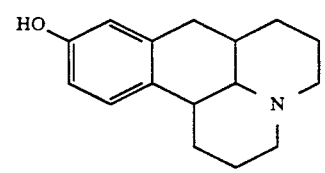

I-3

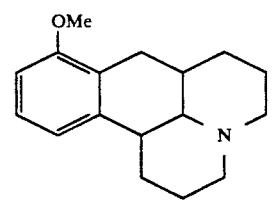

I-4

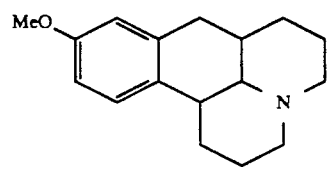

I-5

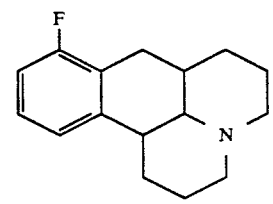

I-6

-continued
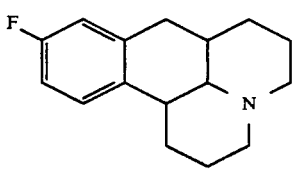 I-7
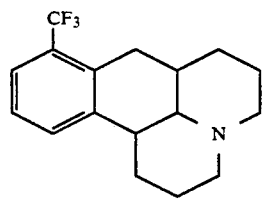 I-8
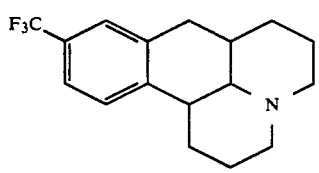 I-9
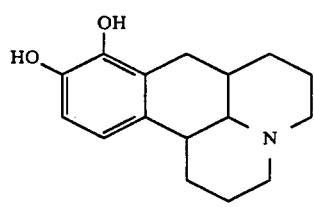 I-10
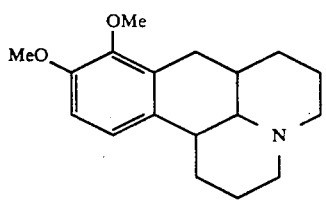 I-11
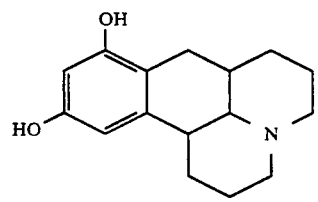 I-12
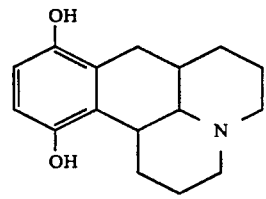 I-13
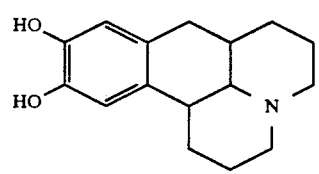 I-14
-continued
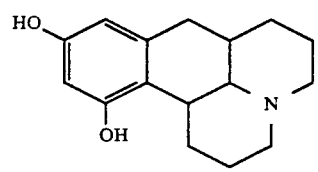 I-15
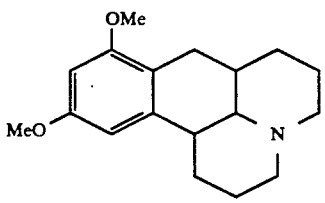 I-16
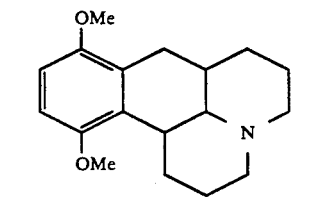 I-17
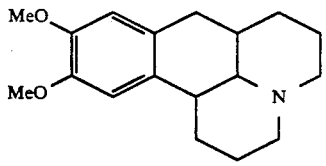 I-18
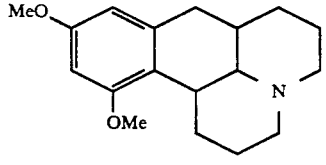 I-19
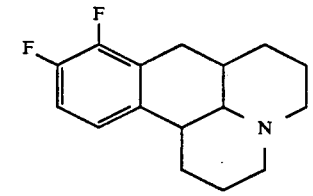 I-20
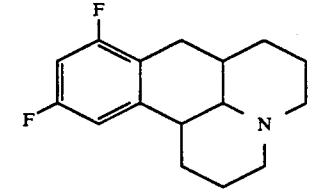 I-21
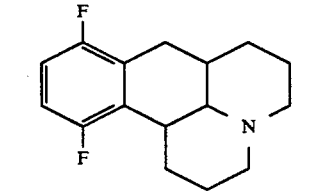 I-22

-continued

I-23 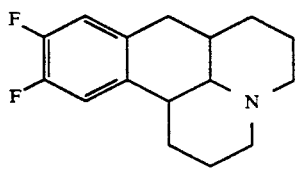

I-24 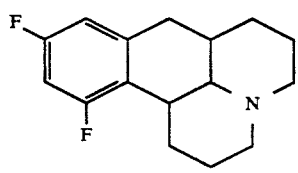

I-25 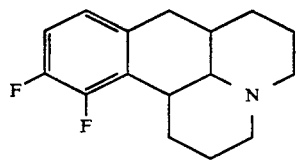

I-26 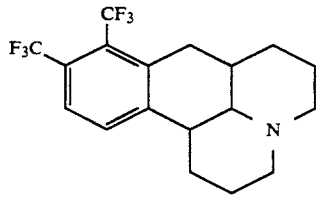

I-27 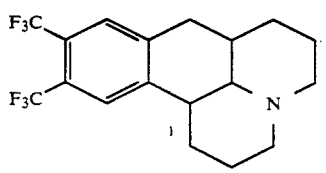

I-28 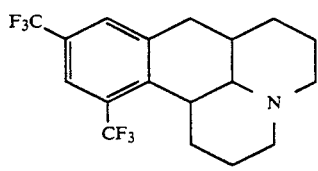

I-29 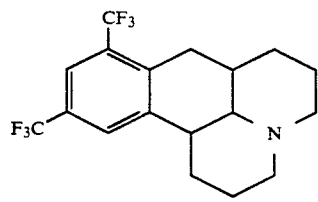

I-30 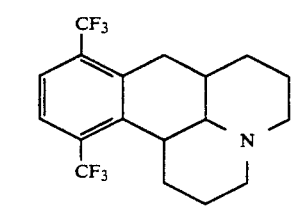

-continued

I-31 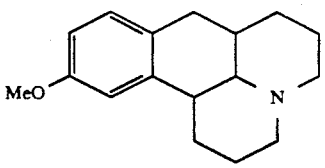

I-32 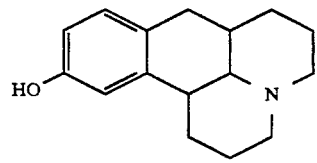

I-33 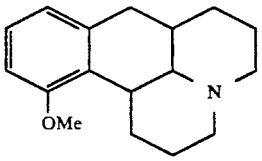

I-34 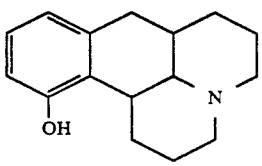

I-35 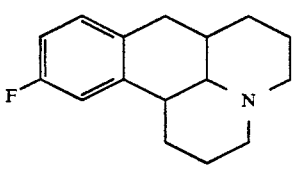

I-36 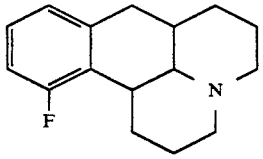

I-37 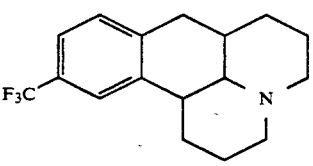

I-38

As a non-limiting example, neuroreceptor specificity and/or neuromodulating activity of alternative stereoisomers of OHNQ compounds according to formula (I) may be readily determined by of one of ordinary skill in the art without undue experimentation, based on the guidance and teachings presented herein. Appropriately functionalized OHNQs according to formula (I) may be synthesized and used in therapeutic, diagnostic and research applications, based on the relationship between the structure and pharmacological activity of the various stereoisomers in each case, based on pharmacological characterization, using known techniques, of a particular OHNQ determined using known methods, without undue experimentation.

Syntheses of OHNQ Compounds According to Formula (I)

OHNQ compounds according to formula (I), in the context of the present invention, may be synthesized using known method steps, based on the teaching and guidance presented herein.

Figure 7A:
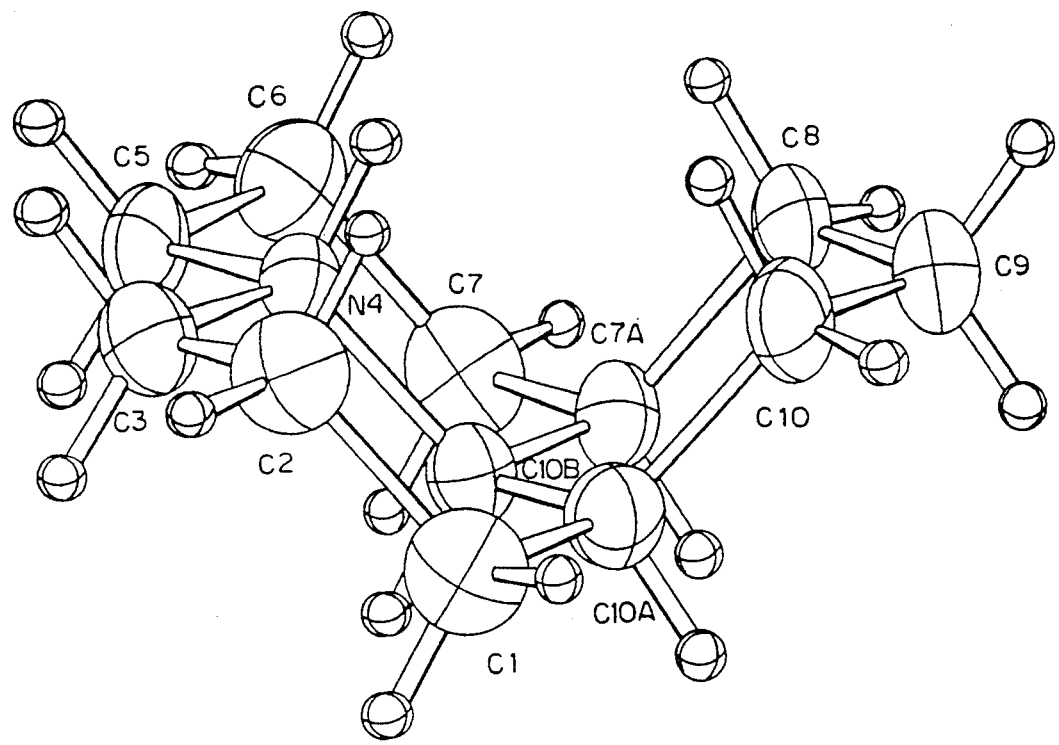
FIGS. 7A–B are computer generated representations of X-ray structures of (cis,cis) tricyclic amine (FIG. 7A) and (cis,cis) OHNQ (FIG. 7B).

As a non-limiting example, OHNQs and derivatives have been now discovered to be synthesized according to the present invention, by unpredictably adapting a synthetic route for tricyclic hexahydrojulolidines (HHJ), used by Mandell et al (*J. Org. Chem.* 29:3067–3068 (1964)) the contents of which is entirely incorporated by reference. Mandell's synthesis, as shown in FIG. 1, involves formation of the enamine of cyclohexanone with pyrrolidine; Michael addition of acrylonitrile to the enamine under conditions which afford the 2,6-bisadduct; and reduction with Raney nickel at high pressure. Mandell concluded from $^1$H NMR data that the main tricyclic hexahydrojuliolidine product was the cis,cis isomer, which was confirmed by the present inventors from an x-ray crystal structure (FIG. 7A). NMR spectral assignments were made from 2D $^{13}$C and $^1$H correlated 300 MHz spectra by the present inventors.

Figure 2:
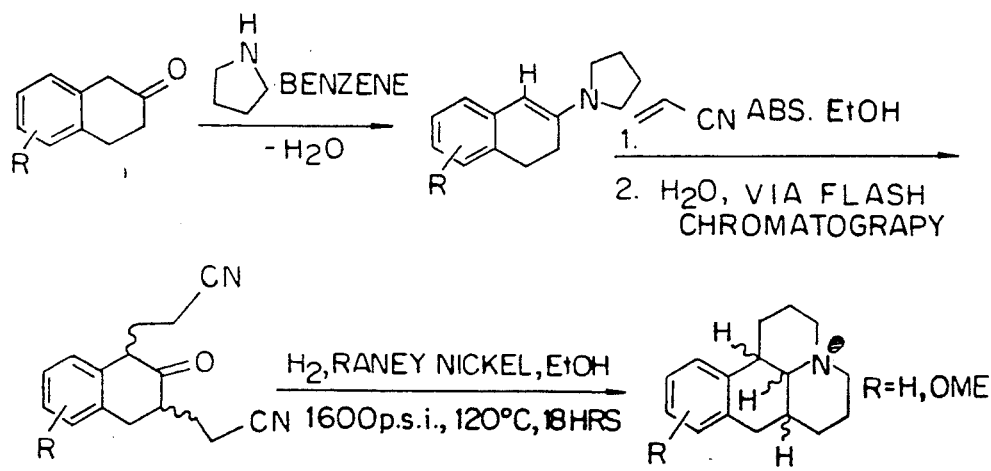
FIG. 2 represents a synthetic scheme for synthesizing an OHNQ of the present invention.

Mandell's synthesis is now discovered to be adaptable in a novel and unexpected manner to prepare OHNQs of formula (I) of the present invention, e.g., if 2-tetralones are substituted for cyclohexanone, as shown in FIG. 2, wherein 2-tetralone and substituted 2-tetralones may be used as starting materials. Experimental conditions for the high pressure Raney nickel reduction may be modified to produce tetracyclic amines in suitable yield as (cis,cis), (trans,trans), (cis,trans), and (trans,cis) stereoisomers, which can be separated chromatographically. Thus, NMR and mass spectral data establishes that tetracyclic OHNQs according to formula (I) of the present invention may be synthesized according to the herein described modifications of Mandell's synthesis.

Figure 3:
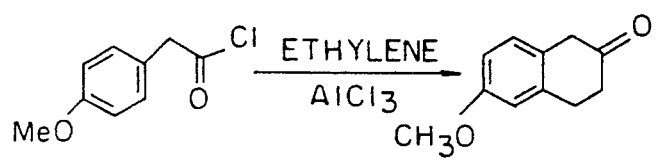
FIG. 3 represents a synthetic scheme for synthesizing a 2-tetralone.

OHNQs according to formula I, with R substituents on the aromatic ring, can be synthesized using conventional steps from the corresponding substituted 2-tetralones, which are available commercially; may be synthesized using known method steps; or can be synthesized from known and readily available compounds using known method steps. As a non-limiting example, one synthetic route to 2-tetralones is shown in FIG. 3, involving reaction of substituted phenylacetyl chlorides with ethylene in the presence of aluminum chloride. Adapting known method steps for this transformation, see Sims, J. J. et al. "6-Methoxy-2-tetralone" *Org. Syn.* 51: 109–112 (1975), p-methoxyphenyl-acetyl chloride has been converted into 6-methoxy-2-tetralone in good yield.

(ii) Pharmacolooical studies

Radioligand binding assays according to known method steps may be used to determine which types of sigma receptors, or other related receptors or associated molecules having a biological function, may be modulated by specific stereoisomers of OHNQ, of the present invention. Such assays may be performed, as a non-limiting example, for Dopamine $D_2$ receptors on mammalian striatal homogenates using ($^3$H)-spiperone in the presence of ketanserin (to inhibit association with some 5-HT receptors and spirodecanone sites), with non-specific binding defined using 10 μm sulpiride. As a further non-limiting subexample, sigma binding assays can be performed on mammalian cell or tissue homogenates, such as from bovine, rat, mouse or rabbit, using an appropriately labeled ligand. Additionally, such assays may be performed on cell lines containing recombinant DNA in which the message for a particular receptor has been inserted.

As a non-limiting subexample, a sigma binding assay can use cerebellar tissue extracts to bind sigma receptor selectively by ($^3$H)-halopendol with spiperone used to inhibit-binding to $D_2$ receptors. As a further non-limiting example, sigma binding assays can be performed using other highly selective, commercially available (from DuPont-New England Nuclear, Boston, Mass.) radio ligands, e.g. ($^3$H)-pentazocine, or ($^3$H)Di-O-Tolyl, guanidine (DTG). These ligands are incubated at 30° C. with tissue (rat liver, rat cerebellum) homogenates for a 45 min period. In these assays, tissue concentrations used a range from 0.1–0.5 mg protein/mL, and radioligand concentrations range from 50 pM–10 μM. Bound and free ligands are separated by rapid filtration under vacuum over GF/B glass fiber filters which have been treated with 0.1% (W/V) polyethyleneimine for a 30 min. period. Filters are dried and counted for ($^3$H)-activity in a liquid scintillation counter. The amount of ligand bound to the tissue receptor is measured with the aid of computer analysis of the data, using the LIGAND or an equivalent algorithm.

Such assays are described in Walker et al. (1990), supra, and are readily performed by one of ordinary skill without undue experimentation.

Specific substituted or unsubstituted OHNQ stereoisomers according to formula (I) of the present invention, are expected to bind a particular sigma receptor with a high degree of specificity, depending on the type of substitution of R groups used as well as depending on the particular stereoisomer, using known method steps.

As a non-limiting example, 11-methoxy OHNQ, according to formula (I) bound more specifically and with a higher affinity to rat cerebellar sigma receptors, than to bovine cerebellar receptors, wherein the 9-methoxy OHNQ is the cis,cis stereoisomer.

As a further non-limiting example, a variety of OHNQs according to formula (I) can be synthesized using the synthetic route outlined in FIG. 2. As a non-limiting sub-example, 11-methoxy OHNQ (i.e., $R^1$=OCH$_3$; and $R^2$, $R^3$ and $R^4$=H) can be prepared from 7-methoxy-2-tetralone. In order to make OHNQs with substituents at other positions on the aromatic ring, the 5, 6, 7, or 8-substituted-2-tetralones can be used as the starting material corresponding to $R^4$, $R^3$, $R^2$ and $R^1$, as the C12, C11, C10 and C9 positions, respectively.

These starting or intermediate tetralones may be prepared from the corresponding ortho- meta- and para-substituted phenylacetic acids using, e.g., a known annulation method, e.g., as shown in FIG. 3, for 6-methoxy-2-tetralone. Similarly, m-substituted phenylacetic acids can be sources of both 5- and 7-substituted tetralones. These phenylacetic acids are known compounds and are readily available from commercial sources (e.g., from Aldrich Chemical Co., Milwaukee, Wis.).

A wide structural range of substituted tetralones which can be used in the synthesis OHNQ compounds of the present invention may be made using conventional method steps, such as from nitrophenylacetic acids, which are widely known and readily available commercially (e.g., from Aldrich Chemical Co., Milwaukee, Wis.). In a preferred embodiment, since the ethylenation/ring closure sequence of FIG. 3 would be inhibited by a nitro substituent on the benzene ring, it may be preferable that the nitrophenylacetic acids are preliminarily converted to the desired X-phenylacetic acids (with X=F, Cl and/or Br being preferred), as a non-limiting example, by well known, synthetic sequences involving reduction of the amino group, diazotization, and Sandmeyer reaction (using Cl or Br) or reaction with $HBF_4$ (using F), prior to the annulation reaction. Alkoxy OHNQs according to formula (I), as alkoxy R groups (with R groups larger than $CH_3$), can similarly be prepared by known method steps. Such compounds are expected to have increased potency as sigma ligands because of enhanced lipophilicity, e.g., where $R^1$, $R^2$, $R^3$ or $R^4$ is an alkyl or substituted alkyl. Preferred, non-limiting examples include at least one of ethyl, n-propyl, i-propyl, n-butyl, 2-butyl, iso-pentyl and 2-phenylethyl. Such substituted OHNQ compounds of the present invention may be prepared most easily from the respective methoxy OHNQs e.g., by hydrolysis to the hydroxy compounds using HBr or $BBr_3$, followed by reaction with the corresponding alkyl halide in the presence of base, according to known reaction steps.

As a non-limiting example of the use of OHNQs of the present invention as modulators of sigma-receptor associated molecules, alkoxy-, and dihydroxy-OHNQs of the present invention are expected to provide receptor modulators and/or ligands, wherein dihydroxy-OHNQs may be used as tetracyclic analogs of dopamine, ADTN and apomorphine. These compounds are also expected to have activity on the serotonin 5-HT-1A receptor, as they structurally resemble the selective agent 8-hydroxy DPAT, as well as other 5HT, dopamine and sigma receptors.

Such compounds may be prepared, as a non-limiting example, from vicinal dialkoxy tetralones. Although 6,7-dimethoxy-2-tetralone is widely known and readily available commercially, it may also preferably be synthesized directly from (3,4-dimethoxyphenyl)-acetic acid (homoveratric acid), using known reaction steps, as has been carried out by the present inventors.

For synthesizing substituted OHNQs of formula (I), the cyclic ether analogue of a 5-, 6-, 7- or 8-, mono-, di-, tri- or tetra-, alkyl or alkoxy-, tetralone, can be used to synthesize the corresponding 12-, 11-, 10-or 9-, mono-, di-, tri or tetra-, alkyl or alkoxy-, OHNQ, according to formula (I).

As a non-limiting example, the cyclic ether analogue of the 7-,8-dimethoxy-tetralone, namely 10,11-methylenedioxy-OHNQ, according to formula (I), can be synthesized similarly from the commercially available (3,4-methylenedioxyphenyl)-acetic acid. Both of these ethers can be used as starting materials for a new tetracyclic dopamine analogue 10,11-dihydroxy-OHNQ (I-14) of the present invention, by treatment with HBr or $BBr_3$. An additional isomeric group of OHNQs can similarly be produced from (2,5-dimethoxyphenyl)-acetic acid.

Mixtures of configurational stereoisomers produced, as a non-limiting example, in the Raney nickel hydrogenation step, may be separated chromatographically using known method steps. As a non-limiting example, flash column chromatography may be used, preferably followed by HPLC. Assigning of stereochemistry can be accomplished using known method steps by comparison of 2D $^{13}C$—$^1H$ COSY NMR spectra with OHNQ or other compounds according to formula I, such as 11-methoxy OHNQ. Each stereoisomeric OHNQ shows a characteristic $^{13}C$ spectral pattern for non-aromatic carbons. Additionally, x-ray crystallography can also be used to determine stereochemistry of OHNQs of the present invention. The determination of stereochemical pattern of the synthesis can alternately be used by known method steps.

In a preferred embodiment, stereochemical assignments can be made which are further based on the presence or absence of the so-called "Bohlmann bands" (see Bohlmann, F. et al. "Konfiguration, synthese und Reactionen der isomeren hexahydrojulolidine" Chem. Ber. 91: 2167-2174 (1958)) in their infrared spectra. These bands, at 2700-2800 $cm^{-1}$, depend on the transoid orientation of the tertiary C—H bonds on the adjacent carbon relative to the lone pair of electrons on nitrogen. In the OHNQ and HHJ series, these bands are present in the cis-cis and trans-trans isomers, but not the cis-trans isomers or trans-cis. A complete high field NMR spectrum also may be useful including 500 and 600 MHz spectra, according to known method steps.

Figure 4:
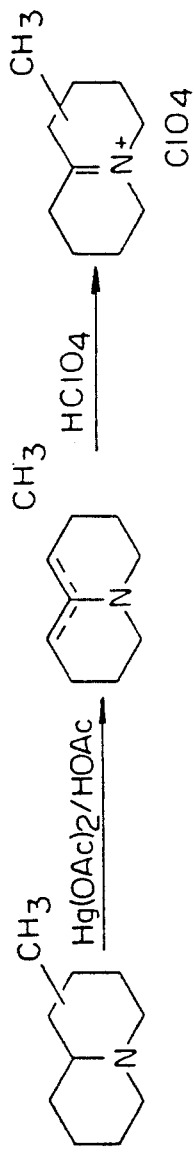
FIG. 4 represents a synthetic scheme for converting dihydro bases to iminium salts.
Figure 5:
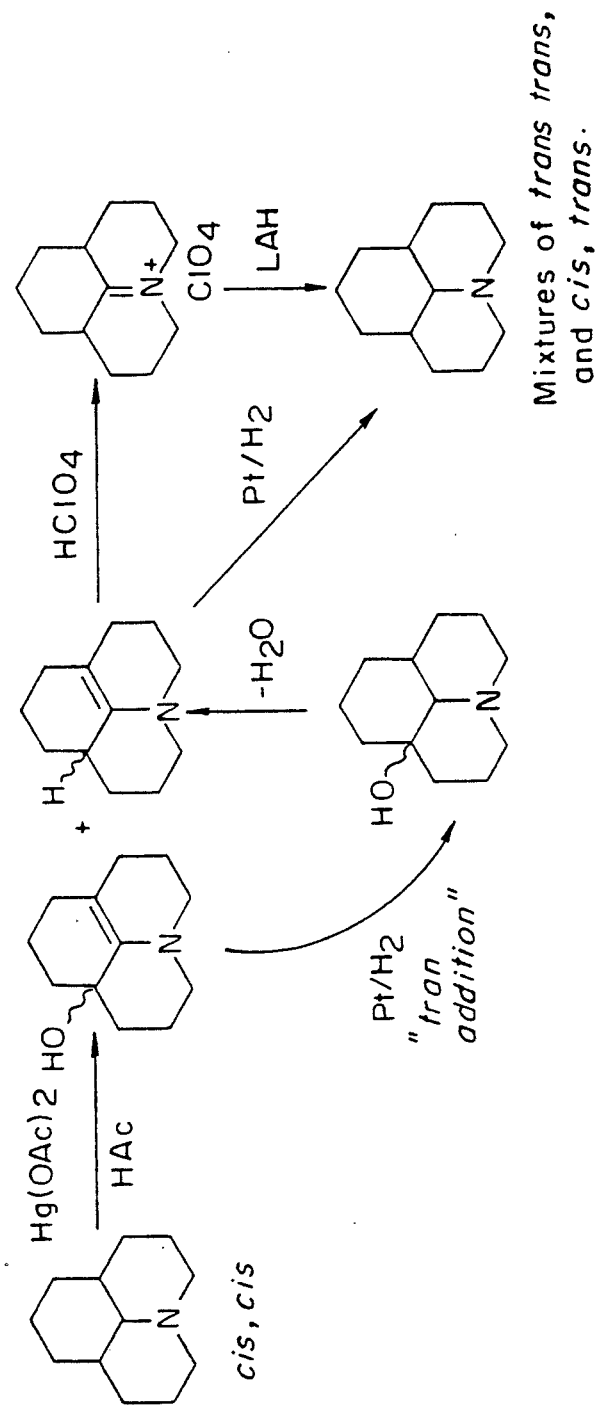
FIG. 5 represents alternative synthetic schemes for converting iminium salts to cis-cis or trans-trans saturated amines.
Figure 6:
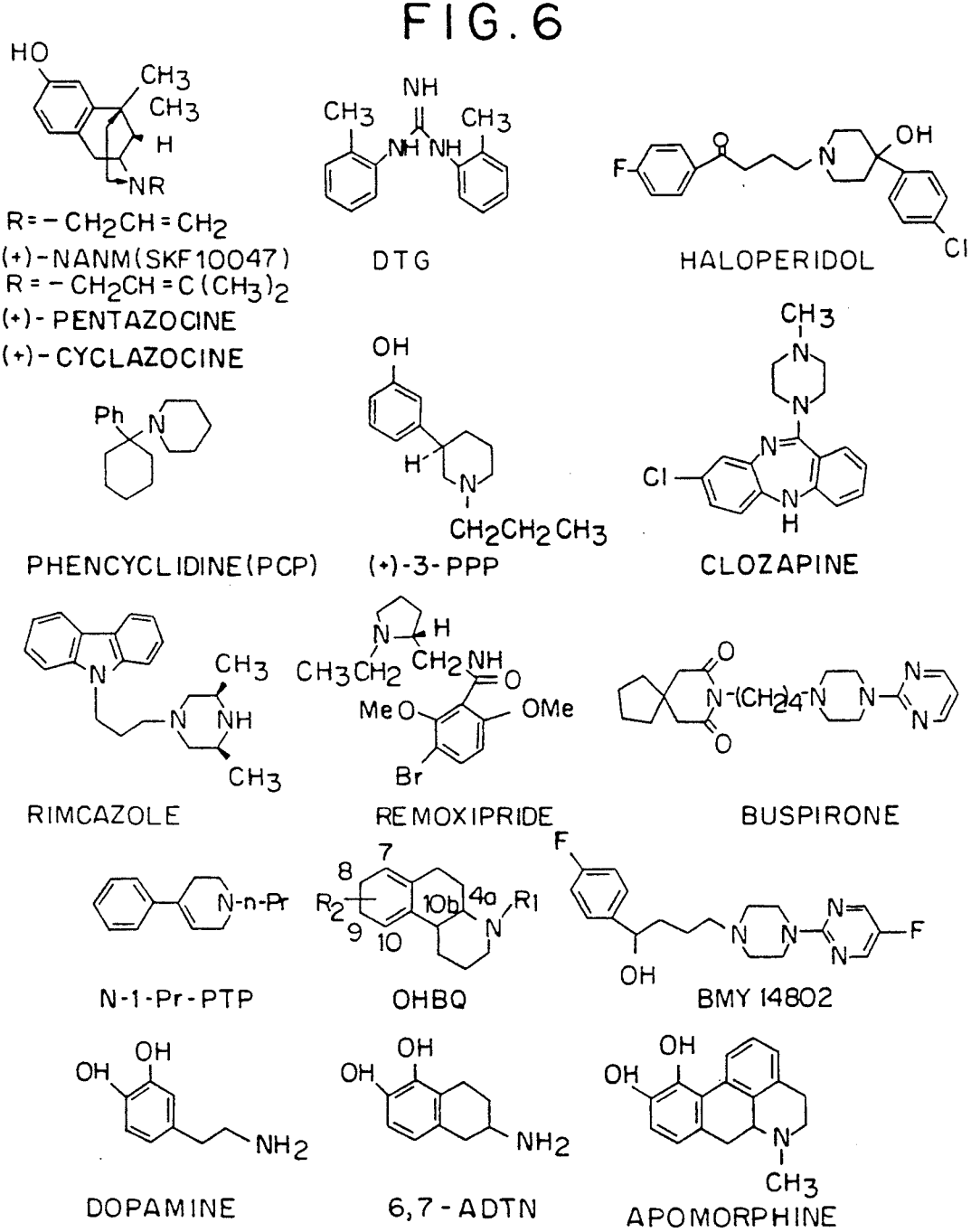
FIG. 6 presents structures of compounds which bind sigma proteins.

Preparation of (trans,trans), or (cis,trans) or (trans,-cis) isomers of OHNQs of the present invention may be accomplished, according a non-limiting example, by epimerizing tertiary amines of (cis,cis) OHNQs at the center adjacent to the nitrogen by dehydrogenation using mercuric acetate according to known methods, (e.g. as presented in Leonard, N. J. et al. *J. Am. Chem. Soc.* 77:439-444 (1955); *J. Am. Chem. Soc.* 78:3457-3462 (1956); and *J. Am. Chem. Soc.* 78:3457-3462 (1956) the contents of which are entirely herein incorporated by reference), followed by either reduction or nucleophilic addition using known method steps. Thus, OHNQs and precursors can be synthesized similarly as in treatment of bicyclic amines, such as quinolizidines, with mercuric acetate, to obtain dehydro bases with a double bond at the bridgehead carbon, which may then be, converted to the corresponding iminium salts, as shown in FIG. 4. These iminium compounds in turn may be readily converted to saturated amines by either catalytic or hydride reduction using known method steps, while alkyl groups may be introduced at the bridgehead position by reaction of the iminium salt with a Grignard reagent according to known method steps. A side reaction to dehydrogenation involves formation of hydroxylated dehydro bases. Analogous to the synthesis of OHNQs of the present invention, reactions of the stereoisomeric tricyclic HHJs with mercuric acetate may provide the cis-cis amine, which can then be used to obtain the dehydrobase and iminium salt, which, upon hydride or catalytic reduction, gives a mixture of the cis-cis and trans-trans saturated amines, as shown in FIG. 5.

Accordingly, as a non-limiting example, a dehydrogenation-reduction route may be used for epimerization of OHNQs at the tertiary carbon next to nitrogen, for preparation of (trans,trans) OHNQs from (cis,cis) isomers, of the Raney nickel hydrogenation sequence of FIG. 2. Such a route may also be used to interconvert cis,trans and trans,cis isomers of OHNQ compounds according to formula (I).

Alternatively, OHNQ compounds of the present invention can be preferably synthesized, such as dialkoxy- and/or dihydroxy-OHNQs, for use, e.g., as neuroreceptor ligands, such as dopamine, 5-HT or sigma ligands for modulation of such receptors and their associated biological activities.

As non-limiting examples, the 10,11-dihydroxy OHNQs (I, $R_2=R_3OH$) latter compounds are tetracyclic analogs of DA, ADTN and apomorphine, which are expected to show DArgic activity. Such compounds may be prepared from vicinal dialkoxy tetralones. For example, 6,7-dimethoxy-2-tetralone has been synthesized from commercially available homoveratric acid according to a literature procedure (Horn et al. *J. Med. Chem.*, 21, 825-828 (1978)), en route to the 10,11-dimethoxy and 10,11-dihydroxy OHNQs (I, $R_2=R_3=OCH_3$ and OH). The latter are obtainable by treatment of the dialkoxy OHNQs with either HBr or $BBr_3$. The cyclic ether analogue of the above compound, namely 10,11,-methylenedioxy-OHNQ, another expected sigma ligand, may be synthesized similarly from the commercially available (3,4-methylenedioxyphenyl)acetic acid.

An isomeric group of OHNQs which do not have substantial dopaminergic activity, but which may have other desirable pharmacological properties, such as modulation of sigma or 5HT receptors, are synthetically available from (2,5-dimethoxyphenyl)acetic acid.

One approach to epimerizing tertiary amines at the center adjacent to the nitrogen is by dehydrogenation using mercuric acetate according to the procedure of Leonard (*J. Am. Chem. Soc.* 77, 439-444 (1955); ibid. 78, 3457-3462 (1956); ibid. 78, 3463-3468 (1956)), followed by either reduction or nucleophilic addition. Treatment of bicyclic amines such as quinolizidines with mercuric acetate affords dehydro bases with the double bond at the bridgehead carbon, which can be converted to the corresponding iminium salts, as shown in Scheme 4. These compounds in turn can be readily converted to saturated amines by either catalytic or hydride reduction, while alkyl groups can be introduced at the bridgehead position by reaction of the iminium salt with a Grignard reagent. A side reaction to dehydrogenation involves formation of hydroxylated dehydro bases. Bohlmann and Arndt (*Chem. Ber.* 91, 2167-2174 (1958)) investigated the reactions of the stereoisomeric tricyclic HHJs with mercuric acetate. From the (cis,cis) amine they obtained the dehydrobase and iminium salt, which upon hydride or catalytic reduction gave a mixture of the (cis,cis) and (trans,trans) saturated amines, as shown in Scheme 5. We have repeated this reaction with the (cis,cis) HHJ and obtained a mixture of products in which hydroxylated products predominate. Although it may be possible to establish conditions to give better yields of dehydro bases using the Leonard reaction, we have obtained much better success by an alternative sequence involving a Polonovski reaction (LaLonde, R. T. et al., *J. Am. Chem. Soc.*, 93, 2501-2506 (1971); Stutz, P. et al. *Tetrahedron Lett.*, 51, 5095-5098 (1973); Mueller, R. H. et al. *J. Org. Chem.* 49, 2217-2231 (1984)).

Thus, treatment of the (cis,cis) tricyclic HHJ with 30% $H_2O_2$ (MCPBA) gives the N-oxide of the amine, as shown in Scheme 6. Significantly higher yields may be obtained using m-chloroperbenzoic acid (MCPBA). Treatment of the N-oxide with acetic anhydride in methylene chloride at 0° C. gives clean conversion to the eneamine, which was characterized by GC/mass spectroscopy and NMR spectroscopy. Catalytic hydrogenation can give about a 1:1 mixture of the (cis,cis) and cis,trans HHJs. Under these conditions, the (cis,cis) OHNQ may react as shown in Scheme 7. It is expected that the Polonovski sequence will give the conjugated eneamine shown rather than alternative isomers. Reduction of this would then give approximately a 1:1 mixture of the starting material and the corresponding cis,trans OHNQ. In order to obtain the (trans,cis) and (trans,trans) OHNQs from the eneamine, one could add dihydrogen in an anti as opposed to a syn manner. One way to achieve this is using lithium in liquid ammonia, such as in the tricyclic model system.

Scheme 4

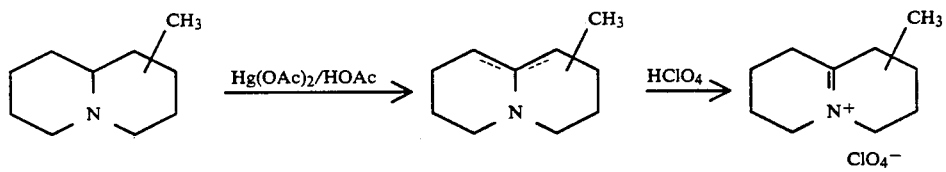

Scheme 5

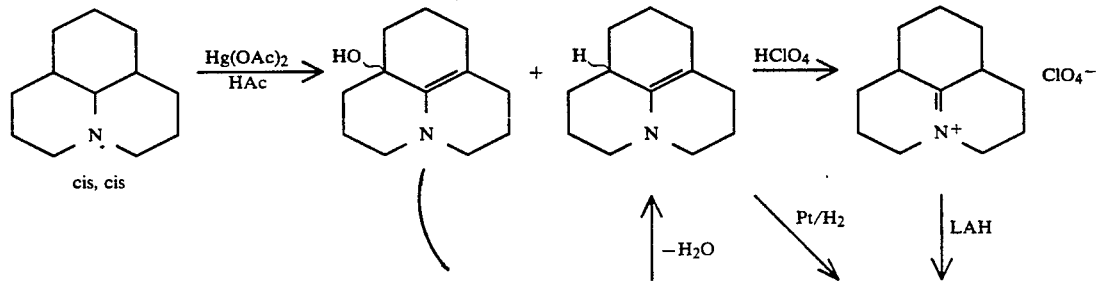

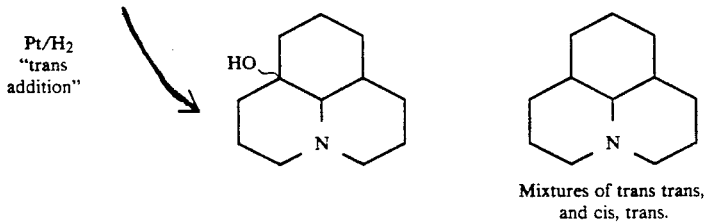

Scheme 6

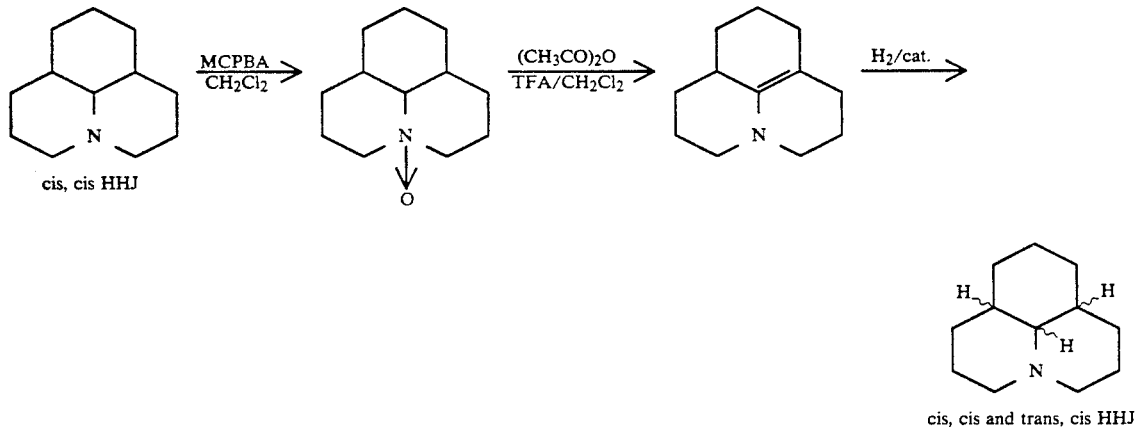

Scheme 7

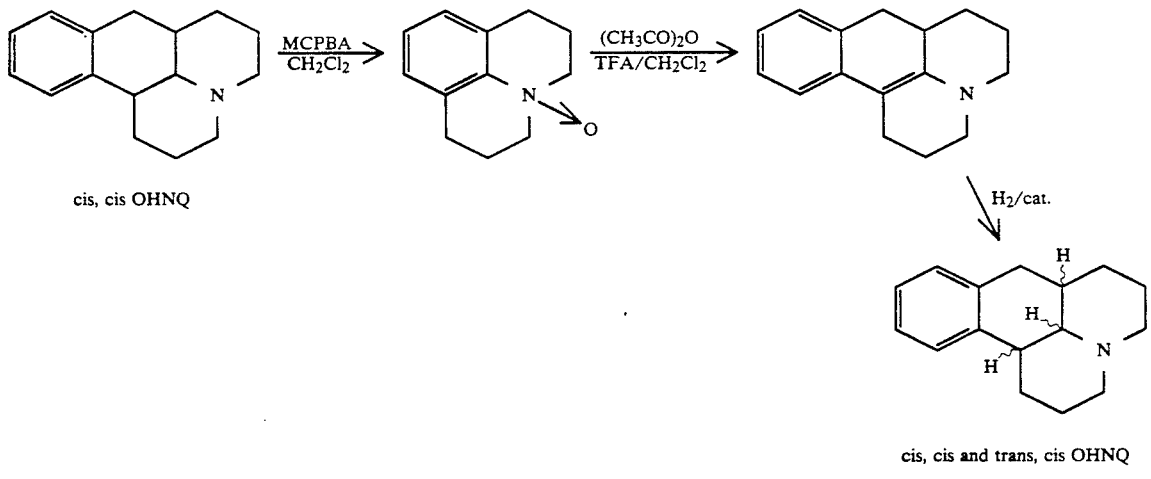

If mixtures of stereoisomers are produced in the reductive cyclization step, these may need to be separate to obtain the individual configurational isomers. As discussed earlier, it has been possible to separated all four diastereomers in the substituted and 11-methoxy OHNQ systems using column chromatography. This is expected to be a general characteristic of this reaction. Mechanistic arguments relating to the stereoselectivity of the Raney nickel reductive cyclization are not particularly compelling. The (trans,trans) diastereomer may also be the second most abundant compound. The data obtained for the unsubstituted and 11-methoxy OHNQ systems indicate that it is expected to be possible to assign the stereochemistry of OHNQs from comparison of their $^{13}C$ and 2D $^{13}C-^{1}H$ COSY 300 MHz NMR spectra with those of the parent compound. In cases where such data do not provide unambiguous stereochemical assignments to new OHNQs, x-ray crystallography may be used to assign stereochemistry. As presented herein, assistance in the stereochemical assignments is provided by the presence or absence of the so-called "Bohlmann bands" in their infrared spectra at 2700–2800 cm$^{-1}$. These bands, which depend on the orientation of the tertiary C—H bonds on carbon next to nitrogen relative to the lone pair of electrons on nitrogen, are present only in the (cis,cis) and (trans,trans) OHNQs, but not in the (cis,trans) or (trans,cis) isomers.

Resolution of racemic OHNQs which show biological activity into their enantiomers by standard techniques should be straightforward, by formation and separation of diastereomeric salts with any of a variety of chiral organic acids, such as dibenzoyltartaric acid and O-methylmandelic acid. If this approach is not satisfactory, resolution may be achieved by passage of racemic OHNQs through commercially available chiral HPLC columns. The absolute configurations of the resolved OHNQs would have to be determined from x-ray crystal structures of salts derived from resolved OHNQs and chiral carboxylic acids of known absolute configuration. From the x-ray structure of such an OHNQ salt, one can directly relate the (unknown) absolute configuration of the OHNQ to the (known) absolute configuration at the stereogenic center(s) of the carboxylic acid.

Resolution of racemic OHNQs, according to formula (I) of the present invention, into enantiomers may be accomplished by known method steps, as a non-limiting example, by formation and separation of diastereomeric salts with any of a variety of chiral organic acids. Non-limiting examples of such chiral organic acids include, but are not limited to, di-O-benzoyltartaric acid and O-methylmandelic acid. Alternatively, such resolution may be achieved by passage of racemic OHNQs through commercially available chiral HPLC columns by known method steps. The absolute configurations of the resolved OHNQs of the present invention may be determined by known method steps from the x-ray crystal structure of a salt derived from one OHNQ enantiomer and a chiral carboxylic acid of a known absolute configuration. Comparison of the x-ray structure of the OHNQ salt to a known compound can directly relate the (unknown) absolute configuration at one or more stereogenic center(s) of the carboxylic acid of the OHNQ to a known chiral center of a chiral carboxylic acid of a known absolute configuration.

Accordingly, OHNQs of formula (I) may be obtained by known method steps in substantially pure form, and further, as specific stereoisomers. Preferably a (cis,cis), (trans,trans), (cis,trans) or (trans,cis) stereoisomer may be obtained as a 70%, 80%, 90% or 95% compound or composition, preferably 92, 94, 97, 98, or 99% of a single stereoisomer of an OHNQ, in accordance with the present invention. Complete separation of stereoisomers has been achieved in the parent unsubstituted OHNQ-methoxy series.

Molecular modeling may be used in the context of the present invention to correlate molecular shape and key functional group features of OHNQs of the present invention for particular biological activities. As non-limiting example, a modeling program, such as MACROMODEL, may be used for empirical minimization of small molecules using Allinger's potentials. Alternatively, in a preferred embodiment, a molecular dynamics simulation type of modeling program may be used. As a non-limiting example, whichever computational algorithm is used, it is preferred that a shell for display of the computational results be used. Examples include the implementation of the Karplus algorithm such as the programs INSIGHT and DISCOVER. Alternatively, additional algorithms may be used to transform the output of the various computational algorithms into the shell file format.

Using such a molecular modeling system, the OHNQ molecule may be easily drawn in a low energy conformation upon which molecular dynamics may be performed with an appropriate number of cycles, until appropriate convergence is obtained. Repetition of such a modeling procedure may then be used to determine if the same or a similar conformational energy minimum is obtained, such that a representative conformational global energy minimum may be defined.

Alternatively, as another non-limiting example, known algorithms maybe used which utilize molecular annealing. See, e.g., Wilson et al. *J. Comput. Chem.* 12:342–349 (1991) and *Drug News Perspect* 4:325–331 (1991) the contents of which are entirely incorporated herein by reference. Preferably, molecular annealing type algorithms are combined with molecular dynamics to provide complementary methods to define global energy minima for the novel ring systems of OHNQ's according to the present invention.

OHNQs of the present invention contain a rigid ring system which is structurally and functionally related to that of known sigma dopamine, serotonin or other receptor ligands, such as are presented in Walker et al, supra. Non-limiting examples include arylpiperidines, including 3-PPP, haloperidol, and BMY 14802. The sigma activity of at least 200 compounds in this general haloperidol/3-PPP class has been tabulated. See Walker et al. *Pharmacol. Rev.* 42:355–737 (1990) and Largent et al. *Proc. Natl. Acad. Sci.* USA 81:4983–4987 (1984) the contents of which references are incorporated entirely herein by reference. Since most of these compounds are relatively flexible from a conformational perspective, the principal correlations, which may be made from these compounds that are relevant to molecular modeling of OHNQs of the present invention, are overall shape and size, and N-aryl distance; these, represent the principal structural features which have been incorporated into existing models of the sigma receptor. Manallack et al. *Eur. J. Pharmacol.* 144:231–235 (1987).

Accordingly, the determination using molecular modeling of OHNQs of the present invention may utilize minimized structures of OHNQs to define surfaces of the molecules and tabulate critical dimensions, which may then, be correlated with similar values for any substituted or unsubstituted OHNQ of the present invention to calculate substituted or unsubstituted OHNQs having the expected greatest biological activity, in terms of both specificity and degree of modulation of sigma receptors.

According to the present invention, OHNQs of formula (I) can be used to modulate sigma and other receptors, including neuroreceptors, for therapeutic and diagnostic applications. One consideration relevant for using OHNQs as receptor modulators, is distinguishing between sigma receptor modulation and related but distinct receptor modulation.

As a non-limiting example, distinguishing between sigma receptor modulation and dopamine modulation may be accomplished using a $D_2$ distinguishing assay, such as a behavioral assay system which discriminates the effects of dopamine $D_2$ antagonists from sigma modulators or agents. A non-limiting example of a $D_2$/sigma distinguishing assay system involves quantification of ingestion of sucrose in a sham-feeding rat, where dopamine plays a critical role in the mediation of this behavior. See Schneider, L. H. et al. *Eur. J. Pharmacol.* 186:61–70 (1990) which is entirely incorporated herein by reference. In this system, all of the ingested sucrose solution is removed from the rat through a gastric fistula; little or no absorption of the carbohydrate occurs, and the animal does not exhibit satiation over the course of the test. The principal factor which compels the animal to maintain ingestion is the sweet taste of the sucrose solution; the involvement of the ascending mesolimbic dopamine system in this effect appears to be manifested as a modulation of the hedonic potency of the orosensory event (sweet taste). See e.g., Schneider, L. H. et al. "Similar effect of raclopride and reduced sucrose concentration on the microstructure of sucrose sham feeding" *Eur. J. Pharmacol.* 186:61–70 (1990), Schneider, L. H. et al. "Infra-additivity of Combined Treatments with Selective D-1 and D-2 Receptor Antagonists" *Brain Res.* 550:122–124 (1991), Murphy, R. B. et al. "Sigma agents do not modulate sucrose reinforcement" *Soc. Neurosci. Abstr.* 16:1028 (1990) which references are incorporated entirely herein by reference.

Motoric components of the ingestive behavior may be differentiated from the "rewarding", sensory components by the use of microstructural analysis, a computer-controlled device which records the time at which each animal licks, to the nearest fractional millisecond. Analysis of licking and ingestive behavior in bursts is monitored through a fixed time test such that sigma agents may influence ingestive behavior either through the motor output systems or through nigrostriatal dopamine systems. The role for sigma sites in motor output systems include those muscles which are associated with licking, biting, and swallowing.

Such a behavioral assay system can be used to distinguish, with peripheral administration of the various selective drugs for sigma receptors, versus other receptor activity where modulation can be distinguished analogously to that for sigma, dopamine or other neurotransmitter receptors, as presented herein. (See Schneider et al., supra.)

As a non-limiting example of D-2 receptor distinguishing, analysis of the mean of the distribution histogram of interlick intervals is based on the fact that occupancy of the sigma does not modulate the sham-feeding of sucrose in the mammals in the same manner as agents which act upon the dopamine D-2 receptor. Therefore, these two properties of a given compound may be readily differentiated by such a behavioral assay to distinguish D-2 and sigma receptor modulation when OHNQs are administered in vivo. Furthermore, the change in the interlick interval distribution is expected to be highly selective for the sigma agents; a wide variety of other drugs selective for other neuroreceptors do not produce this distribution shift.

Thus, as a non-limiting example, peripheral administration in mammals of OHNQs of the present invention, using the behavioral assay of microstructure quantification in the sham-feeding rat, as presented herein, may be used to determine dose dependencies for sigma receptors under varied dose conditions to determine if sigma receptor modulating effects occur. The significance of these effects will then be assessed by analyses of variance followed by the use of appropriate, nonparametric post-hoc tests, such as the Tukey's test.

One or more other known behavioral assays, such as stereotyped behavior, rotation contralateral to a lesion of the dopaminergic systems, conditioned avoidance-response and analysis of brain regions after drug administration for catecholamines and their metabolites by HPLC, as non-limiting examples, may also be used according to the present invention. One or more of these assays can be used on OHNQs of the present invention to determine behavioral quantitative and qualitative effects in vivo.

Having now generally described the invention, the same will be further understood by reference to certain specific examples which are included herein for purposes of illustration only and are not intended to be limiting.

EXAMPLE I

Synthesis of OHNQs According to formula I

OHNQs according to Formula I were synthesized according to the present invention by unpredictable modification of a route originally used by Mandell et al (*J. Org. Chem.* 29:3067–3068 (1964)) for the synthesis of tricyclic hexahydrojulolidines.

Mandell's synthesis was unexpectedly discovered to be adaptable to make OHNQs of the present invention by using 2-tetralones substituted for cyclohexanone, as shown in FIG. 2, wherein 2-tetralone and 7-methoxy-2-tetralone were used as starting materials to provide OHNQs, wherein $R^1$, $R^2$, $R^3$ and $R^4$ are hydrogen (for 9C, C10, C11 and C12 (I-1)) or wherein R1, $R^3$ and $R^4$ are each hydrogen (for C10, C9 and C12 (I-5)) and $R^2$ is methoxy for C11, respectively. Using the reformulation of Mandell's synthesis, as shown in FIG. 2, OHNQs as presented above are synthesized by conversion to an eneamine from the 2-tetralone with pyrrolidine; Michael addition of acrylonitrile to the enamine under conditions which afford the 2,6-bisadduct; and reduction with Raney nickel at high pressure.

Figure 7B:
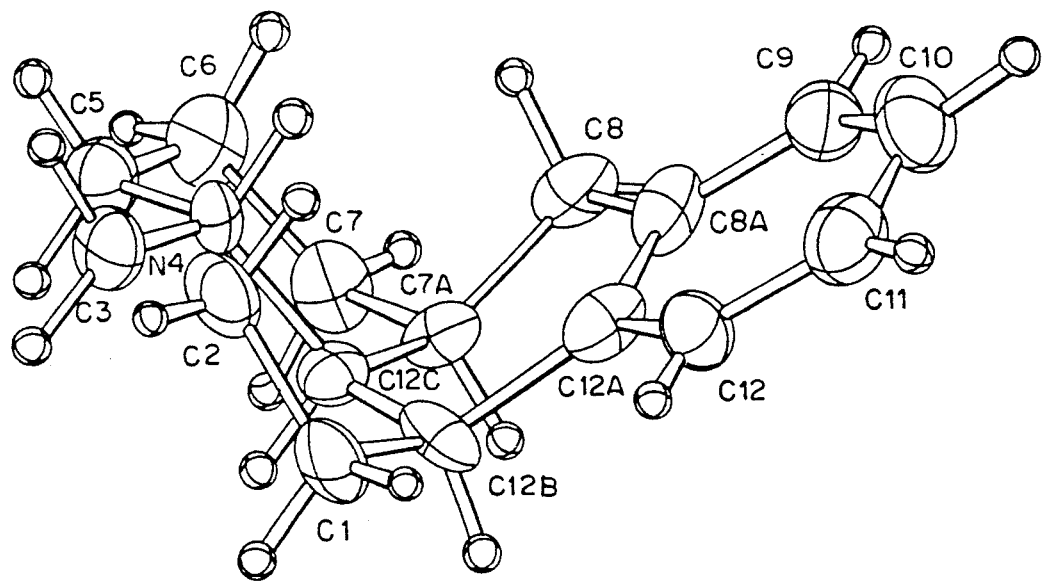
Figure 8A:
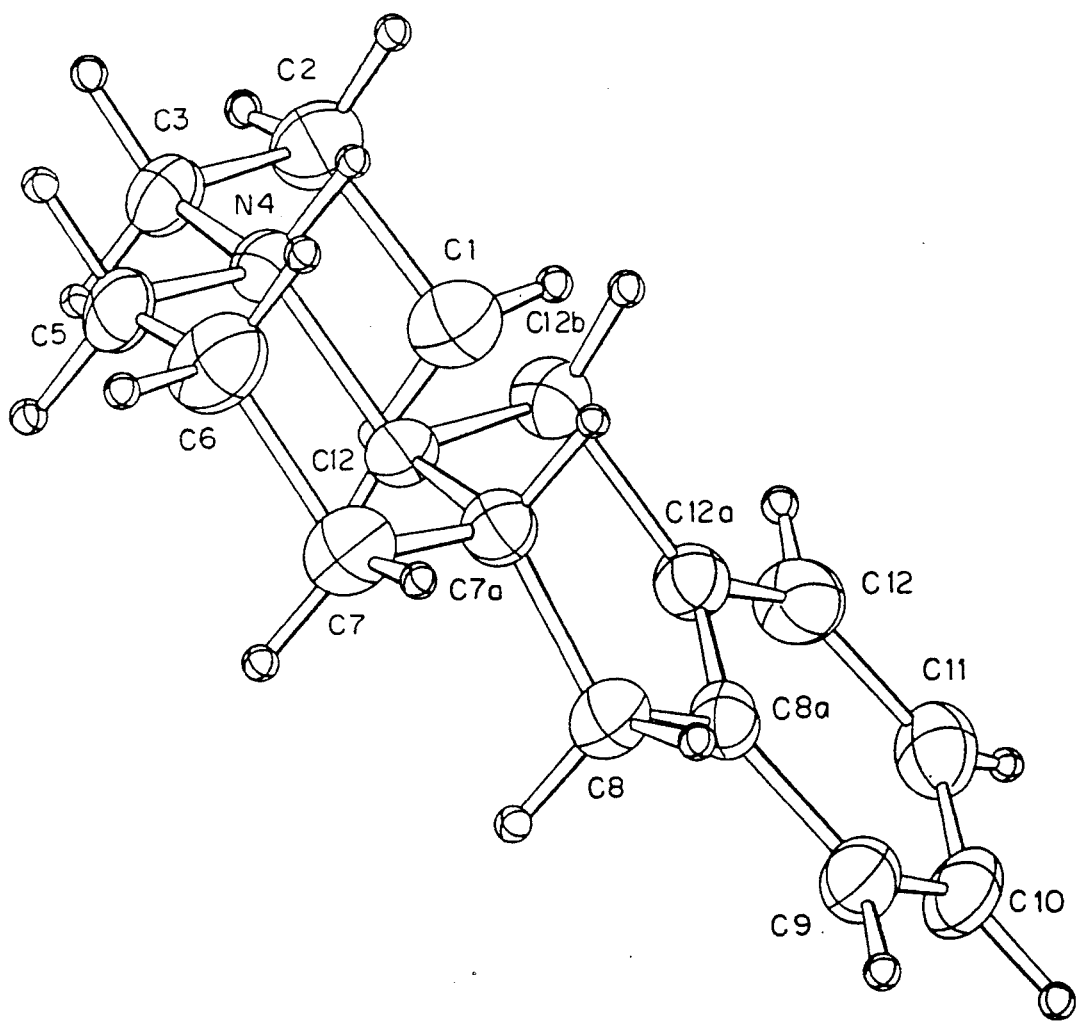
FIGS. 8A–B are computer generated representations of X-ray structures (trans,trans) (FIG. 8A) and (trans,cis) (FIG. 8B) OHNQ.
Figure 8B:
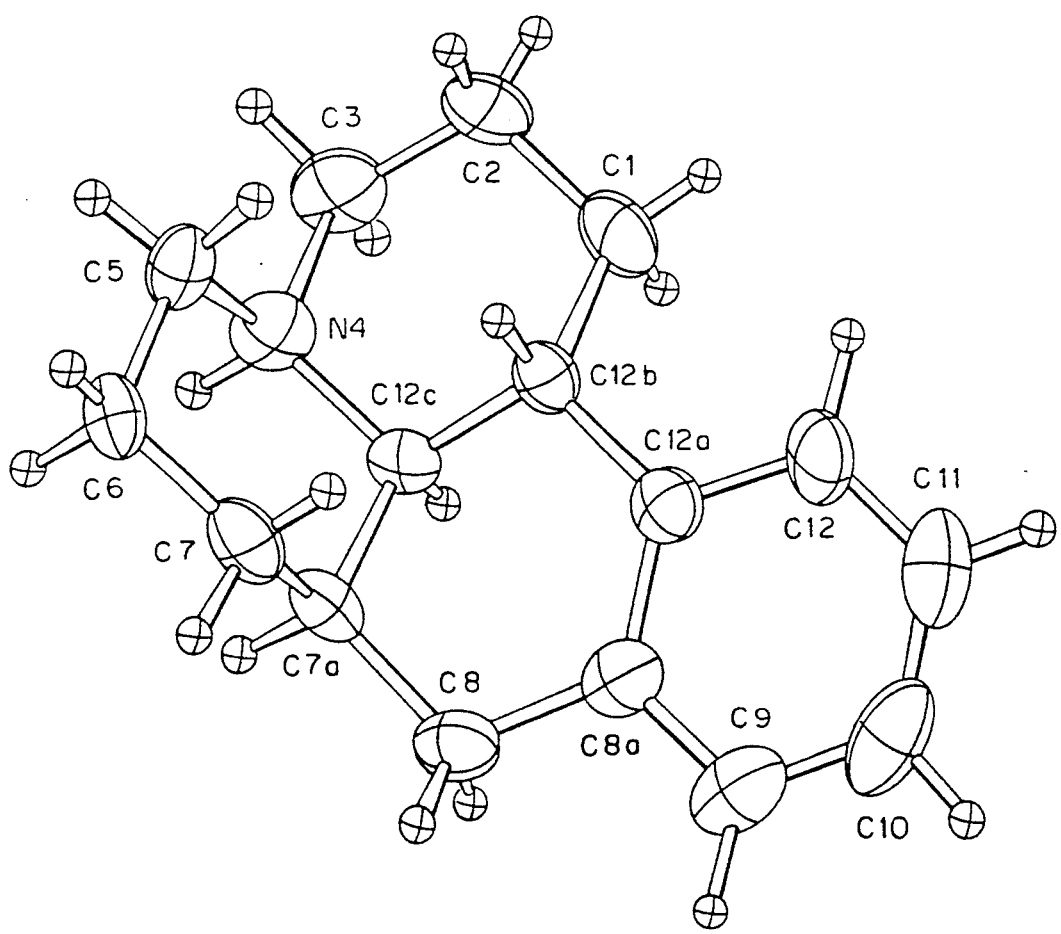
Figure 9A:
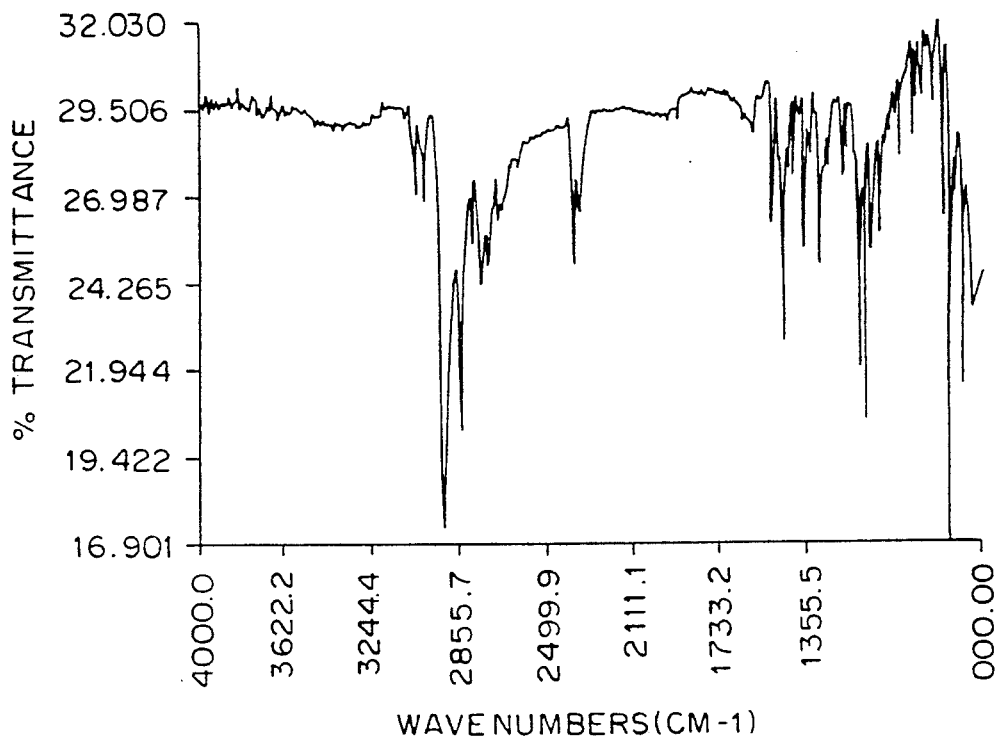
FIGS. 9A–D are graphic representations of IR spectra for stereoisomers of OHNQ.
Figure 9B:
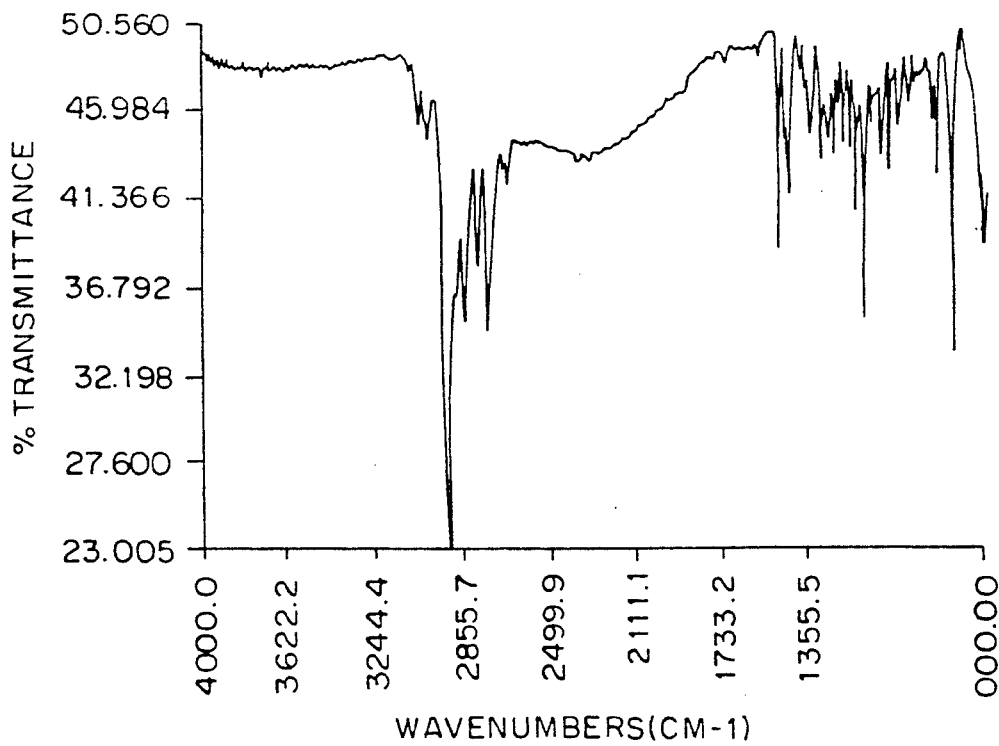
Figure 9C:
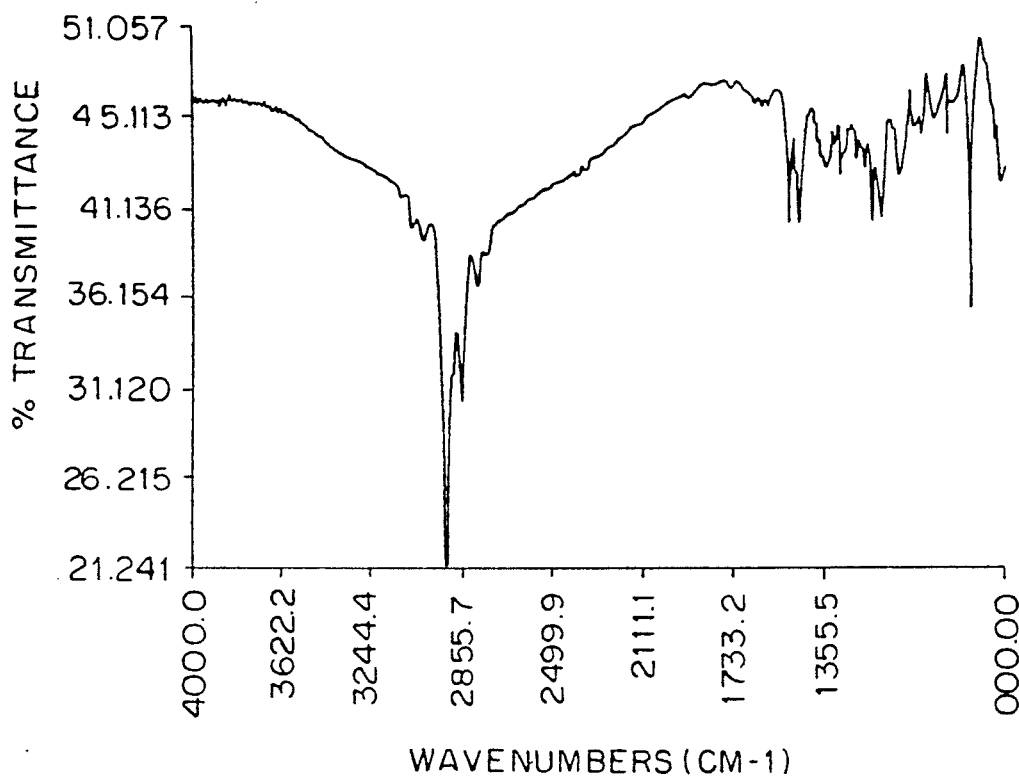
Figure 9D:
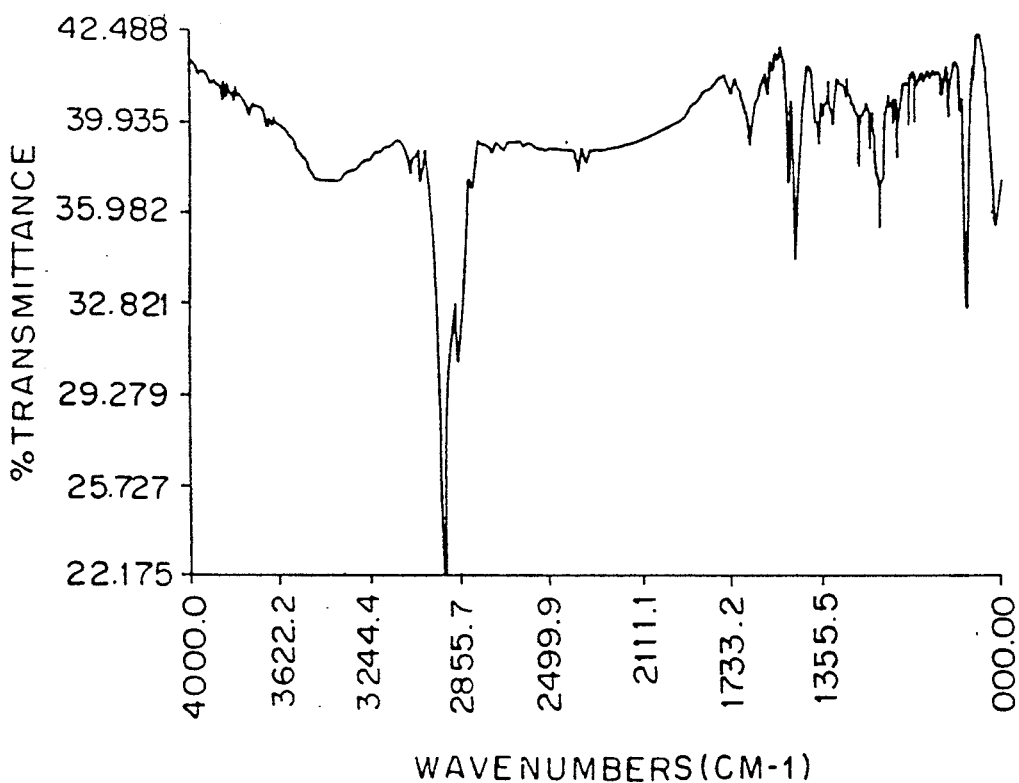

Experimental conditions for the high pressure Raney nickel reduction were modified as shown in FIG. 2 and provided a 50–60% OHNQ yield. The structures of these compounds were confirmed from $^1H$ and $^{13}C$ as well as 2D $^{13}C$—$^1H$ correlated NMR spectral data as OHNQ and 11-methoxy OHNQ respectively. The x-ray structure of the major product in the unsubstituted system shows it is the (cis,cis) compound (FIG. 7B) as (cis,cis) OHNQ, with the minor products of OHNQ with the same molecular mass as the (cis,cis) OHNQ according to GC/MS data also being produced as the (trans,cis), (cis,trans) and (trans,trans) isomers. The assignments were confirmed by $^1H$ and $^{13}C$ NMR spectra, and x-ray structures for the (trans,trans) and (trans,cis) isomers (FIGS. 8A and 8B). Additional structural correlations may include the presence or absence of so-called Bohlmann bands in the infrared spectra, at ca. 2700 cm$^{-1}$. These bands are present only in the (cis,cis) and (trans,trans) isomers, where there is a hydrogen anti to the long pair of electrons in nitrogen.

IR spectra for (cis,cis), (trans,trans), (cis,trans), and (trans,cis) OHNQ are presented in FIGS. 9A–D, respectively.

OHNQs with substituents on the aromatic ring were synthesized from the corresponding substituted 2-tetralones, which are available commercially, or were synthesized from available compounds including reaction of substituted phenylacetyl chlorides with ethylene in the presence of aluminum chloride, as presented in FIG. 3. Adapting a literature procedure for this transformation, Sims, J. J. et al. *Org. Syn.* 51:109–112 (1975), p-methoxyphenyl-acetyl chloride was converted into 6-methoxy-2-tetralone in good yield. 5-, 6-, 7-, or 8-methoxy substituted OHNQ, as 9-, 10-, 11- or 12-methoxy OHNQ, respectively were obtained in good yield.

Figure 10:
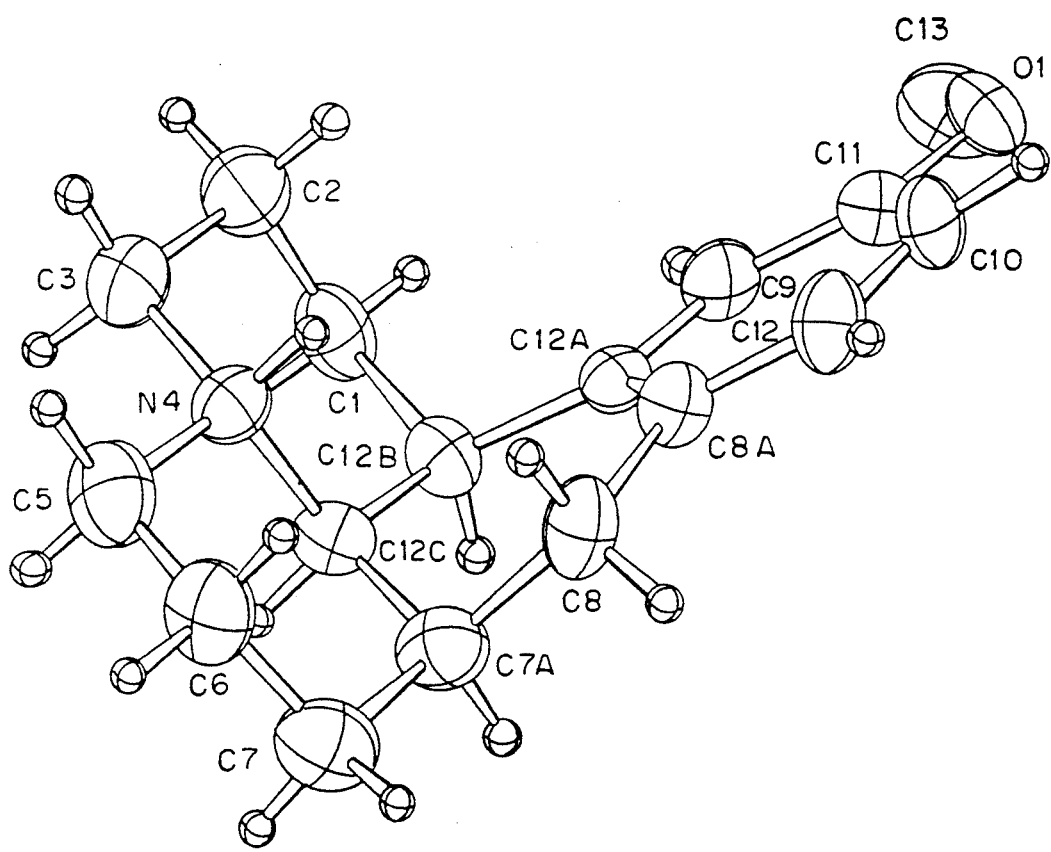
FIG. 10 is a computer generated representation of an X-ray structure of (cis,cis) 11-methoxy OHNQ.

$^{13}C$-NMR (APT) chemical shifts of unsubstituted and 11-methoxy OHNQs (nonaromatic carbons only) are presented in Table I, wherein CH and CH$_3$ resonances are underlined. FIG. 10 shows the X-ray crystallography structure of (cis,cis) 11-methoxy OHNQ.

TABLE I $^{13}$C NMR (APT) Chemical shifts of unsubstituted and 11-methoxy OHNQs (non-aromatic carbons only). CH and CH$_3$ resonances are underlined.

| | Unsubstituted OHNQs | | | | | | | | | |
|---|---|---|---|---|---|---|---|---|---|---|
| cis, cis | 64.4 | 57.8 | 57.4 | 38.3 | 33.3 | 30.1 | 29.5 | 28.2 | 21.2 | 20.6 |
| trans, trans | 69.1 | 56.3 | 56.2 | 41.4 | 36.9 | 36.0 | 32.2 | 29.6 | 25.5 | 24.7 |
| cis, trans | 62.7 | 54.6 | 46.6 | 35.4 | 33.9 | 30.1 | 29.7 | 25.3 | 24.8 | 21.5 |
| trans, cis | 60.7 | 54.9 | 45.6 | 40.0 | 37.2 | 33.3 | 31.2 | 26.1 | 24.1 | 18.8 |
| | 11-Methoxy-OHNQs | | | | | | | | | |
| cis, cis | 64.2 | 57.7 | 57.3 | 38.3 | 33.3 | 29.4 | 29.5 | 29.0 | 21.1 | 20.5 55.2 (OMe) |
| trans, trans | 69.1 | 56.3 | 56.2 | 42.2 | 36.2 | 36.1 | 32.2 | 29.7 | 25.6 | 24.8 55.2 (OMe) |
| cis, trans | 62.6 | 54.6 | 46.6 | 34.6 | 34.2 | 30.2 | 29.9 | 25.3 | 25.0 | 21.5 55.2 (OMe) |
| trans, cis | 60.7 | 55.0 | 45.6 | 40.4 | 36.4 | 33.3 | 31.2 | 26.1 | 24.1 | 18.8 55.2 (OMe) |

EXAMPLE 2

Pharmacology Studies on OHNQ of the Present Invention

Radioligand binding assays were performed on the tricyclic (cis-cis) hexahydrojulolidine (HHJ), the parent tetracyclic (cis,cis) OHNQ (I-1) and 9-methoxy OHNQ (I-4), for binding to D$_2$ and sigma receptors synthesized according to Example 1. The D$_2$ assays were performed on bovine striatal homogenates using 0.50 nM ($^3$H)-spiperone in the presence of 250 μM ketanserin (to inhibit association with some 5-HT receptors and spirodecanone sites), with non-specific binding defined using 10 μM sulpiride according to known methods. The sigma binding assay was performed on bovine and rat cerebellar homogenates using 2.0 nM ($^3$H)-haloperidol in the presence of 25 nM spiperone (to inhibit association with D2 dopamine receptors); non-specific binding was defined in the presence of 1 μM unlabeled haloperidol. The HHJ did not exhibit binding to sigma sites in both rat and bovine cerebellar preparations. The 11-methoxy OHNQ exhibited weak sigma binding in the bovine preparation (IC$_{50}$=1.5 μM), and had a considerably stronger binding (IC$_{50}$=300 μM) to rat cerebellar membranes. The latter potency is on the order of that observed for (+)-NaMM, (+)-3-PPP, as well as cis-fused tricyclic octahydrobenzo-(f) quinolines with hydroxyl groups on the aromatic ring. Sigma receptor assays on rat brain preparations using ($^3$H)-DTG and ($^3$H)-Pentazocine as the radiolabels are performed with good results. The unsubstituted (trans,trans) OHNQ shows high affinity to sigma receptors in solubilized rat liver preparations, with IC$_{50}$=87 nM, vs 157 nM in crude liver homogenates. Additional assays have been performed for D-1 activity (using ($^3$H)-SCH23390), and for α-1 and α-2 activity as well as several 5-HT subtypes (5-HT-1-a, 5-HT-3, 5-HT uptake site). Several of these compounds, most notably the (trans,trans) unsubstituted OHNQ and (trans,trans) 11-methoxy OHNQ, show modest but selective activity at 5-HT-2 and D-2 receptor sites. This activity is not unlike that of the atypical neuroleptic clozapine. These results demonstrate that stereoisomers of OHNQs according to formula (I) are expected to provide clinically significant receptor modulation of sigma and 5-HT-2 receptors, as well as dopamine D-2 receptors.

EXAMPLE 3

Synthesis of OHNQs According to Formula I

A variety of substituted OHNQs are synthesized using the synthetic route outlined in FIG. 2, as presented in Example 1. These OHNQs, for which x-ray crystal structures were also obtained and for which OHNQs are characterized spectroscopically, are prepared from appropriate 5, 6, 7, or 8-substituted-2-tetralones. These are used to synthesize the corresponding 12, 11, 10 or 9 substituted OHNQ, respectively, including 9-, 10-dihydroxy; 9-hydroxy, 10-hydroxy; 9-methoxy; 9-, 10-dimethoxy OHNQ in turn are prepared from the corresponding ortho, meta and para substituted phenylacetic acids using the annulation method shown in FIG. 3, such as 6-methoxy-2-tetralone to make 10-methoxy OHNQ. The meta-substituted phenylacetic acids are sources of both the 5- and 7-substituted tetralones.

Substituted tetralones are synthesized from the three nitrophenylacetic acids, which are commercially available. Since the ethylenation/ring closure sequence of FIG. 3 may be inhibited by a nitro substituent on the benzene ring, the nitrophenylacetic acids are converted to the desired X-phenylacetic acids (particularly with X=F, Cl, CF$_3$ and Br) by a known reaction sequence, including the reduction to the amino group, diazotization, and Sandmeyer reaction (when using Cl, Br) or reaction with HBF$_4$ (when using F) prior to the annulation reaction. Alkoxy OHNQs with OR groups at various aromatic positions with R groups including CH$_3$, C$_2$H$_5$, n-C$_3$H$_7$, 2-C$_4$H$_9$, iso-C$_5$H$_{11}$, n-C$_4$H$_9$, n-C$_5$H$_{11}$, C$_6$H$_{13}$ and C$_2$H$_4$-phenyl are synthesized. Such compounds are expected to have increased potency as sigma ligands because of enhanced lipophilicity particularly with at least one of R$^1$, R$^2$, R$^3$ or R$^4$=ethoxy, n-propoxy, n-butoxy, and 2-phenylethoxy. These OHNQ compounds may be prepared from the respective methoxy OHNQs by hydrolysis to the hydroxy compounds using HBr or BBr$_3$, followed by reaction with the corresponding alkyl halide in the presence of base, using known method steps.

10,11-dialkoxy- and dihydroxy-OHNQs are also synthesized as sigma and dopamine receptor ligands. These compounds are prepared from vicinal dialkoxy tetralones. 6,7-dimethoxy-2-tetralone is commercially available and is used as obtained, or as synthesized directly from (3,4-dimethoxyphenyl)-acetic acid (homoveratric acid). The cyclic ether analogue of the above compound, namely 10,11-methylenedioxy-OHNQ, is synthesized similarly from the commercially available (3,4-methylenedioxyphenyl)-acetic acid. Both of these ethers are converted to a dopamine analogue 10,11-dihydroxy-OHNQ by treatment with either HBr or BBr$_3$ using known steps. Isomeric groups of OHNQs are made from (2,5-dimethoxyphenyl)-acetic acid.

The mixture of stereoisomers, produced in the Raney nickel hydrogenation step, is first separated chromatographically to give the configurational isomers, including major products and minor products, using flash column chromatography. A full separation of all the stereoisomers may also be achieved by HPLC. Stereochemistry of the OHNQs is assigned by comparison of 2D $^{13}C$—$^1H$ COSY MMR spectra with those of the parent compound and 11-methoxy OHNQs (the various isomers have very distinct spectra in the non-aromatic region, except for the methoxy group) synthesized as presented in Example 1 above. Additionally, x-ray crystallography may be used to confirm the stereochemistry of synthesized and isolated OHNQs.

Assistance with the product stereochemical assignments is provided by the presence or absence of the so-called "Bohlmann bands" Bohlmann, F. et al. *Chem. Ber.* 91:2167–2174 (1958) in the infrared spectra of OHNQs. These bands at 2700–2800 $cm^{-1}$ depend on the orientation of the C—H bonds on carbon relative to the lone pair of electrons on nitrogen. In OHNQs of the present invention synthesized as above, these bands are present in the (cis-cis) and (trans-trans) isomers, but not the (cis-trans) or (trans-cis) isomers.

EXAMPLE 4

Receptor Binding Pharmacology Studies of ONHQs of the Present Invention

The following protocols may be used as part of receptor binding pharmacology studies of substituted or unsubstituted OHNQs of the present invention.

Tissue preparation

Crude tissue homogenates are prepared by the following general procedure. Frozen tissue is thawed and homogenized in a buffer containing 50 mM Tris-HCl, 120 mM NaCl, 1 mM $MgCl_2$, and 5 mM KCl, pH 8.0. This tissue suspension is sedimented at 100,000×g for a 30 min. period. Following centrifugation, the supernatant is discarded and the resultant pellet is resuspended in the same buffer solution, and respun as previously described. The resultant pellet is suspended once more in the same buffer to give a final protein concentration of ca. 500 μg/mL, determined according to the standard procedure of Lowry or by dye-binding (Bradford) assay.

Sigma Binding Assays

Ten to twenty point assays are performed in triplicate using either 4 nM ($^3H$)-haloperidol, 4 nM ($^3H$)-DTG or 0.4 nM ($^3H$)-DTG (New England Nuclear) as radiolabels, on rat liver, rat cerebellar or bovine cerebellar homogenates. The concentration of the displacing agent generally ranges between 0.2 nM and 64 μM in a final volume of 2 mL. Non-specific binding is defined by the presence of 1 μM unlabeled haloperidol. Spiperone at a concentration of 25 nM is added in the assays performed with ($^3H$)-haloperidol in order to block D2 receptor sites. The buffer system employed is as in the tissue preparation as presented herein. Incubation is carried out for one hour at room temperature after addition of the tissue. Samples are rapidly filtered through Schleicher and Schuell #32 glass filters presoaked with 0.1% polyethyleneimine, on a 24-position cell harvester (Brandel). The filters are washed with ice-cold 10 mM Tris buffer, pH 7.7, and then placed in 2 mL of scintillation fluid. Radioactivity is counted the following day at 40% efficiency.

Docamine (D 2) Assays

Ten to twenty point assays are performed in triplicate using 2.0 nM ($^3H$)-raclopride (New England Nuclear). Alternatively or additionally, 0.25 nM ($^3H$)-spiperone (New England Nuclear) is used as the radiolabel. A rat or bovine striatal homogenate as presented is used, with a tissue concentration less than 100 μg/ml of Bradford assayed protein in the assay tubes (final volume). The concentration of the displacing agent generally ranges between 0.2 nM and 64 μM in a final volume of 2.00 mL. Non-specific binding is defined by the presence of 10 μM racemic sulpiride or 500 nM raclopride. The buffer system used for this assay is Tris-HCl, pH 7.4, containing 140 mM NaCl, 5 mM KCl, and 5 mM EDTA (disodium salt). Incubation is carried out for one hour at room temperature (28° C. after addition of the tissue. Samples are rapidly filtered through Schleicher and Schuell #32 glass filters presoaked with 0.1% polyethyleneimine, on a 24-position cell harvester (Brandel). The filters are washed with ice-cold 10 mM Tris buffer, pH 7.7, and then placed in 2 mL of scintillation fluid. Radioactivity is counted the following day at ~40% efficiency.

Dopamine (D-1) Assays

Ten to twenty point assays are performed in triplicate using 0.5 nM ($^3H$)-SCH23390 (New England Nuclear). A rat or bovine striatal homogenate as presented herein is used, with a tissue concentration less than 100 mg/ml of Bradford assayed protein in the assay tubes (final volume). The concentration of the displacing agent generally ranges between 0.2 nM and 64 μM in a final volume of 2.00 mL. Non-specific binding is defined by the presence of 200 nM piflutixol or 500 nM SCH23390. The buffer system used for this assay is Tris-HCl, pH 7.40, containing 140 mM NaCl, 5 mM KCl, and 5 mM EDTA (disodium salt), 0.05% (w/v) ascorbic acid, and 50 μM 5-HT (to inhibit possible association of SCH23390 with 5-HT receptors), and is freshly prepared. Incubation is carried out for one hour at 30° C. after addition of the tissue. Samples are rapidly filtered through Schleicher and Schuell #32 glass filters presoaked with 0.1% polyethyleneimine, on a 24-position cell harvester (Brandel). The filters are washed with ice-cold 10 mM Tris buffer, pH 7.7, and then placed in 2 mL of scintillation fluid. Radioactivity is counted the following day at 40% efficiency.

Other dopamine receptor assays

Assays for activity of agents on D-3 or D-4 receptors, are performed by known method steps using cloned cell lines in which these receptors have been expressed. Todd, R. D. et al. *Proc. Natl. Acad. Sci.* 86:10134–10138 (1989); Chio, C. L. et al. *Nature* 343:266–269 (1990); Zhou, Q. Y. et al. *Nature* 347:146–151 (1990); Sokoloff et al. *Nature* 347:146–151 (1990); Van Tol, H. M. et al. *Nature* 350:614–619 (1991); and Sunaghara, R. K. et al. *Nature* 350:614–619 (1991), such as using a radiolabeled clozapine for the D4 site. Van Tol, H. M. et al. *Nature* 350:610–619 (1991). The above references are herein entirely incorporated by reference. Based upon agonist selectivities for this site, such assays are herein provided based on published information.

Other receptor assays

Receptor assays are performed on OHNQs according to Formula I for α-1 and α-2 receptors using ($^3H$)-prazosin and ($^3H$)-yohimbine, respectively; β-1 and β-2 receptors, using a nonselective label (as ($^3H$)-dihydroalprenolol and the ICI compounds to distinguish the subtypes; M-1 and M-2 receptors, using ($^3H$)-QNB and pirenzipine to distinguish the subtypes, and various 5-HT subtypes, including in particular 5-HT-1a receptors (using ($^3H$)-8-OH DPAT) and the 5-HT uptake site (using ($^3H$)-paroxetine), as shown herein.

Data analysis

The algorithms LIGAND, in the original NIH version written for the IBM PC, and/or EBDA version (Elsevier) may be used to transform displacements to saturation curves, and to perform multisite analysis to estimate $K_i$ values. Multisite analysis yields more than one site, displacements containing a considerable number of points (up to 50) are performed to achieve an appropriate degree of statistical precision.

EXAMPLE 5

Behavioral Studies Using OHNQs According to Formula I

Differentiation of sigma and dopamine activities are provided by a behavioral assay system which effectively discriminates the effects of dopamine D-2 antagonists from sigma agents. The assay system involves quantification of ingestion of sucrose in the sham-feeding rat.

This behavioral system demonstrates that the motoric components of the ingestive behavior may be differentiated from the "rewarding", sensory components by the use of microstructural analysis. This consists of the use of a computer-controlled device which records the time at which each animal licks, to the nearest fractional millisecond. This then allows analysis of licking and ingestive behavior in bursts through a 30-minute test. This behavioral differentiation provides an assay demonstrating sigma agents that influence ingestive behavior either through the motor output systems or through nigrostriatal dopamine systems.

Using this behavioral assay system, with peripheral administration of the various selective drugs, rats (N=6) received 20% sucrose during a 30-min test, such that there was no effect of the sigma agents (+)-SKF 10,047 (5 mg/kg, i.p.; SKF) or BMY 14802 (4 mg/kg, i.p.; BMY) depending upon the volume of the sucrose solution which was ingested. In contrast, haloperidol (0.1 mg/kg, i.p.; HAL), a drug which has high affinity for both the sigma and the D-2 receptor, produced a highly significant reduction ($33.7 \pm 2.7$ ml vs $15 \pm 2.7$ ml; $p < 0.001$) in sham intake of the sucrose solution. However, microstructural analysis of the ingestive behavior demonstrated a significant decrease of interlick intervals in the range 0-250 msec as well as a smaller mean lick cluster size in animals which had received BMY but not SKF or HAL. These changes are attributed to a shift in the mean of the distribution histogram of interlick intervals. The occupancy of the sigma site does not modulate the sham-feeding of sucrose in the rat in the same manner as agents which act upon the dopamine D-2 receptor; therefore, these two properties of a given compound are expected to be readily differentiated by this behavioral assay. Furthermore, the change in the interlick interval distribution is quite selective for the sigma agents; a wide variety of other drugs selective for other neuroreceptors does not produce this distribution shift. The shift in interlick interval distribution is expected to arise from occupancy of hindbrain sigma sites, possibly in the reticular formation, which are involved in definition of the lick rate in the rat. Administration of the sigma compounds intraventricularly, or into various tissue sites (nucleus, accumbens, striatum) did not produce the shift in lick rate distribution; the hindbrain regions involved in lick rate definition are expected to be more accessible to peripherally-administered agents owing to the porous nature of the blood-brain barrier in this region.

OHNQ compounds are examined by peripheral administration in the rat of these agents, using the behavioral paradigm of microstructure quantification in the sham-feeding rat. Small groups of animals (N=6-8) are used for determination of dose dependencies will be performed at log steps of the compounds, and ANOVAS will be performed across the dose conditions to determine if effects occur. The significance of these effects is then assessed by the use of appropriate, non-parametric post-hoc tests including the Tukey's test. Good results are expected, wherein dose dependencies in vivo are obtained for various OHNQs of the present invention as sigma receptor modulators.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the contents of the references cited within the references cited herein are also entirely incorporated by reference.

Reference to known method steps, conventional methods steps, and known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the generic concept of the present invention. Therefore, such adaptations and modifications are intended to be comprehended within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein.

LITERATURE CITED

1. Seeman, P. (1980) "Brain Dopamine Receptors", *Pharmacol. Rev.* 32, 229.
2. Walker, J. M. et al. (1990) "Sigma Receptors: Biology and Function", *Pharmacol. Rev.* 42, 355-737.
3. Snyder, S. H. et al. (1989) "Receptor mechanisms in antipsychotic drug action: focus on sigma receptors" *J. Neuro-psychiatry* 1, 7-15; Largent, B. L. et al. (1988) "Novel antipsychotic drugs share high affinity for sigma receptors" *Eur. J. Pharmacol.* (1988) 155, 345.
4. Martin, W. R. et al. (1976) "The effects of morphine- and nalorphine-like drugs in the nondependent and morphine dependent chronic spinal dog" *J. Pharmacol. Exp. Therap.* 197, 517-532.
5. Su, T.-P. (1981) "Psychotomimetic opiate binding: specific binding of ($^3$H) SKF-10047 to etorphine-inaccessible sites in guinea pig brain" *Eur. J. Pharmacol.* 75, 81-82; Su, T.-P. (1982) "Evidence for sigma opioid receptor binding of ($^3$H)-SKF-10047 to etorphine inaccessible sites in guinea pig brain" *J. Pharmacol. Exp. Therap.* 223, 284-290.
6. Mendelsohn, L. G. et al. (1985) "Sigma opioid receptor: characterization and co-identity with the phencyclidine receptor. *J. Pharmacol. Exp. Therap.* 233, 597–602; Zukin, S. R. et al. (1984) "Behavioral and biochemical stereoselectivity of sigma opiate/PCP receptors" *Brain Res.* 294, 174–177.

10. Gundlach, A. L. et al. (1985) "Phencyclidine and sigma-opiate receptors in brain-biochemical and autoradiographic differentiation" *Eur. J. Pharm.* 113, 465–466; Largent, B. L. et al. (1984) "Psychotomimetic opiate receptors labeled and visualized with (+)-($^3$H)-3-(3-hydroxyphenyl)-N-(1-propyl)piperidine" *Neurobiol.* 81, 4983–4987; Gundlach, A. L. et al. (1986) "Autoradiographic localization of sigma-receptor binding sites in guinea pig and rat central nervous systems with (+)- ($^3$H)-3-(3-hydroxyphenyl)-N-(1-propyl)piperidine" *J. Neurosci.* 6, 1757–1770.

11. McLean, S. et al. (1988) "Autoradiographic visualization of haloperidol-sensitive sigma receptors in guinea-pig brain" *Neuroscience* 25, 159–269; Aaronsen, L. M. et al. (1989) "Phencyclidine and sigma receptors in rat spinal cord: binding characterization and quantitative autoradiography" *Synapse* 4, 1–10.

12. Yang, Z. W. et al. (1989) "Expression of (+)-3-PPP binding sites in the PC12 pheochromocytoma cell line" *Eur. J. Pharm.* 164, 607–610; Hellewell, S. C. et al. (1990) "A sigma-like binding site in rat pheochromocytoma (PC12) cells: decreased affinity for (+)-benzomorphans and lower molecular weight suggest a different sigma receptor form from that in guinea pig brain" *Brain Res.* 527, 244–253; Bowen, W. D. et al. (1989) "Evidence for a multi-site model of the rat brain sigma receptor" *Eur. J. Pharmacol.* 163, 309–318. See also Musacchio, J. M. et al. (1989) "Dextromorphan and sigma ligands: common sites but diverse effects" *Life Scie.* 45, 1721–1732.

13. Ehrlich, G. K. et al. (1992) "Affinity purification of the sigma receptor/binding site from rat liver" *J. Neurochem.*, in press.

14. Ferris, C. D. et al. (1991) "Sigma Receptors: From Molecule to Man" *J. Neurochem.* 57, 729–737.

15. Kaiser, C. et al. (1991) "Sigma Receptor Ligands: Function and Activity" *Neurotransmissions* (Research Biochemicals Incorporated) Vol. VII, No. 1, 1–5.

16. Su, T.-P. et al. (1986) "Endogenous ligands for sigma opioid receptors in the brain ("sigmaphin"): evidence from binding assays" *Life Sci.* 38, 2199–2210;

17. Tam, S. W. et al. (1984) "Sigma-opiates and certain anti-psychotic drugs mutually inhibit (+)-($^3$H)- SKF10047 and ($^3$H)-haloperidol binding in guinea pig membranes" *Proc. Natl. Acad. Sci.* USA 81, 5618–5621.

18. Carlsson, A. (1983) "Dopamine receptor agonists: intrinsic activity versus state of receptor" *J. Neural Trausm.* 57, 309; Hacksell, U. et al. (1981) "3-Phenylpiperidines. Central dopamine-autoreceptor stimulating activity" *J. Med. Chem.* 24, 1475; Johansson, A. M. et al. (1985) "Novel dopamine receptor agonists and antagonists with preferential action on autoreceptors" *J. Med. Chem.* 28, 1049–1053; Svensson, K. et al. (1986) "A homologous series of N-alkylated cis-(+) (1S,2R)-5-methoxy-1-methyl-2-aminotetralines: central dopamine receptor antagonists showing profiles ranging from classical antagonism to selectivity for autoreceptors" *J. Neural Transm.* 65, 29–38.

19. Largent, B. L. et al. (1984) "Psychotomimetic opiate receptors labeled and visualized with (+)-($^3$H)-3-(3-hydroxyphenyl)-N-(1-propyl)piperidine" *Proc. Natl. Acad. Sci.* USA 81, 4983–4987.

20. Largent, B. L. et al. (1987) "Structural determinants of sigma receptor affinity" *Mol Pharmacol.* 32, 772–784.

21. Itzhak, Y. et al. (1991) "Characterization of N-methyl-4-phenyl-1,2,3,6-tetrahydropyridine (MPTP) binding sites in C57BL/6 mouse brain: mutual effects of monoamine oxidase inhibitors and sigma ligands on MPTP and sigma binding sites" *Mol. Pharmacol.* 39, 385–393.

22. Bowen, W. D. et al. (1990) "Metabolites of haloperidol display preferential activity at sigma receptors compared to dopamine D-2 receptors" *Dur. J. Pharm.* 177, 111–118.

23. Wikstrom, H. et al. (1987) "N-substituted-1,2,3,4,4a,5,6-10b-octahydrobenzo(f)quinol ines and 3-phenylpiperidines: effects on central dopamine and sigma receptors" *J. Med. Chem.* 30, 2169–2174; Van de Waterbeemd, H. et al. (1987) "Quantitative structure-activity relationships and eudismic analyses of the presynaptic dopaminergic activity and Dopamine D2 and sigma receptor affinities of 3 (3-hydroxyphenyl)piperidines and octahydrobenzo(f)quinolines" ibid. 30, 2175–2181.

24. Katerinopoulos, H. (1984) Ph. D. Dissertation, New York Univ.

25. Luke, M. (1987) Senior Honors Thesis, New York University.

27. Mandell, L. et al. (1961) "The synthesis of dl-Matridine" *J. Am. Chem. Soc.* 83, 1766; Mandell, L. et al. (1963) "The Syntheses of Tricyclic Systems with Nitrogen at a Bridgehead" *J. Org. Chem.* 28, 3440–3442; Mandell, L. et al "A convenient synthesis of tricyclic 2-quinolizidones" *J. Org. Chem.* 29:3067–3068 (1964) Mandell, L. et al. (1965) "The total syntheses of d,l-Matrine and d,l-Leontine" *J. Am. Chem. Soc.* 87, 5234–5236.

28. Sims, J. J. et al. (1975) "6-Methoxy-2-tetralone" *Org. Syn.* 51, 109–112.

30. Kavanaugh, M. P. et al. (1988) "Identification of the binding subunit of the sigma-type opiate receptor by photoaffinity labeling with 1-(4-azido-2-methyl(6-$^3$H)phenyl)-3-(2-methyl(4,6-$^3$H)phenyl guanidine" *Proc. Natl. Acad. Sci.* USA 85, 2844–2848.

32. Leonard, N. J. et al. (1955) "Unsaturated Amines. III. Introduction of α,β-Unsaturation by means of Mercuric Acetate: Δ$^{9,10}$-Dehydroquinolizidine" *J. Am. Chem. Soc.* 77, 439–444; Leonard, N. J. et al. (1956) "Unsaturated Amines. VII. Introduction of α,β-unsaturation by means of mercuric acetate: methylquinolizidines" ibid. 78, 3457–3462; Leonard, N. J. et al. (1956) "Unsaturated amines. VIII. Dehydrogenation and hydroxylation of 1-methyldecahydroquinjoline by means of mercuric acetate" ibid. 78, 3463–3468.

33. Bohlmann, F. et al. (1958) "Konfiguration, synthese und Reactionen der isomeren hexahydrojulolidine" *Chem. Ber.* 91, 2167–2174.

34. Wilson, S. R. et al. (1991) "Applications of simulated annealing to the conformational analysis of flexible molecules" *J. Comput. Chem.* 12, 342–349; Wilson, S. R. (1991) "Molecular modeling in drug design" *Drug News Perspect.* 4, 325–331.

35. Manallack, D. T. et al. (1987) "Quantitative conformational analyses predict distinct receptor sites for PCP-like and sigma drugs" *Eur. J. Pharmacol.* 144, 231–235; Manallack, D. T. et al. (1988) "Receptor site topographies for phencyclidine-like and sigma drugs: predictions from quantitative conformational, electrostatic potential, and radioreceptor analyses" *Mol. Pharmacol.* 34, 863–879.

36. Todd, R. D. et al. (1989) "Cloning of ligand-specific cell lines via gene transfer; identification of a D-2 dopamine receptor subtype" *Proc. Natl. Acad. Sci.* 86, 10134–10138.

37. Chio, C. L. et al. (1990) "A second molecular form of D-2 dopamine receptor in rat and bovine caudate nucleus" *Nature* 343, 266–269.

38. Zhou, Q. Y. et al. (1990) "Cloning and expression of human and rat D-1 dopamine receptors" *Nature* 347, 76–80.

39. Sokloff, P. et al. (1990) "Molecular cloning and characterization of a novel dopamine receptor D-3 as a target for neuroleptics" *Nature* 347, 146–151.

40. Van Tol, H. M. et al. (1991) "Cloning of the gene for a human D-4 receptor with high affinity for the antipsychotic clozapine" *Nature* 350, 610–614.

41. Sunaghara, R. K. et al. (1991) "Cloning of the gene for a human dopamine D-5 receptor with higher affinity for dopamine than D-1"*Nature* 350, 614–619.

42. Waddington, J. L. et al. (1989) "Drugs acting on brain dopamine receptors; a conceptual reevaluation five years after the first selective D-1 antagonist" *Pharmacol. Therap.* 43, 1–52.

43. Schneider, L. H. et al. (1990) "Similar effect of raclopride and reduced sucrose concentration on the microstructure of sucrose sham feeding" *Dur. J. Pharmacol.* 186, 61–70.

44. Schneider, L. H. et al. (1991) "Infra-additivity of combined treatments with selective D-1 and D-2 receptor antagonists" *Brain Res.* 550, 122–124.

45. Murphy, R. B. et al. (1990) "Sigma agents do not modulate sucrose reinforcement" *Soc. Neurosci. Abstr.* 16, 1028.

What is claimed is:

1. An octahydronaphthoquinolizine compound or stereoisomer of a compound of formula (I):

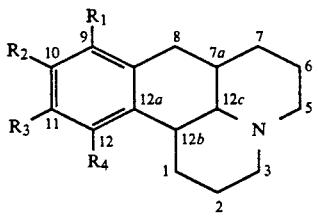

wherein $R^1$, $R^2$, $R^3$ and $R^4$ are the same or different, as hydrogen, hydroxy, fluoro, trifluoromethyl, or a substituted or unsubstituted $C_{1-10}$ alkoxy which can be substituted with alkyl or phenyl groups, or a pharmaceutically acceptable ester, ether, sulfate, carbonate, glucuronide, cyclodextrin complex or salt thereof.

2. A compound according to claim 1, wherein at least one of $R^1$, $R^2$, $R^3$ or $R^4$ is hydroxy.

3. A compound according to claim 1, wherein at least one of $R^1$, $R^2$, $R^3$ or $R^4$ is fluoro, chloro, or bromo.

4. A compound according to claim 1, wherein at least one of $R^1$, $R^2$, $R^3$ or $R^4$ is a $C_{1-10}$ alkoxy.

5. A compound according to claim 4, wherein the $C_{1-10}$ alkoxy is a substituted hydroxy or phenyl $C_{1-10}$ alkoxy.

6. A compound according to claim 1, selected from octahydronaphthoquinolizine, 9-hydroxy-octahydronaphthoquinolizine, 10-hydroxy-octahydronaphthoquinolizine, 11-hydroxy-octahydronaphthoquinolizine, 9-methoxy-octahydronaphthoquinolizine, 10-methoxy-octahydronaphthoquinolizine, 11-methoxy-octahydronaphthoquinolizine, 9-fluoro-ctahydronaphthoquinolizine, 10-fluoro-octahydronaphthoquinolizine, 11-fluoro-octahydronaphbhoquinolizine, 10-trifluromethyl-octahydronaphthoquinolizine, 9-trifluoromethyl octahydronaphthoquinolizine, 9-,10-dihydroxy-octahydronaphthoquinolizine, 10-,11-dihydroxy-octahydronaphthoquinolizine, 9-,10-dimethoxy-octahydronaphthoquinolizine, 10-,11-dimethoxy-octahydronaphthoquinolizine, 9-,10-difluoro-octahydronaphthoquinolizine, and 9-,11-di-trifluoromethoxy octahydronaphthoquinolizine.

7. A compound according to claim 1, wherein said stereoisomer is selected from trans,trans; cis,cis; trans,-cis and cis,trans.

8. A pharmaceutical composition for use in situ and in vivo for modulating receptor related biological activities comprising a compound according to claim 1, and a pharmaceutically acceptable carrier.

9. A method for treating a subject suffering from a receptor related pathology, comprising administering an effective receptor modulating amount of a compound according to claim 1.

10. A method according to claim 9, wherein said compound is administered to provide said compound in an amount ranging from about 0.1 to 30 mg/kg.

11. A method according to claim 10, wherein said compound is administered to provide said compound in an amount ranging from about 0.15 to 10 mg/kg.

12. A method according to claim 9, wherein said animal is selected from a mammal and a bird.

13. A method according to claim 12, wherein said mammal is a human.

14. A method according to claim 9, wherein said pathology is dystonia, tardive dyskinesia, schizophrenia, Huntington's Chorea, Gilles de la Tourette's Syndrome or Parkinson's disease.

* * * * *